US012577214B2

(12) United States Patent
Dabros et al.

(10) Patent No.: US 12,577,214 B2
(45) Date of Patent: Mar. 17, 2026

(54) POLYMORPHS OF BIS(FLUOROALKYL)-1,4-BENZODIAZEPINONE COMPOUNDS AND USES THEREOF

(71) Applicant: Bristol-Myers Squibb Company, Princeton, NJ (US)

(72) Inventors: Marta Dabros, Foster City, CA (US); Joshua Engstrom, Spotswood, NJ (US); Daniel Richard Roberts, Robbinsville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 455 days.

(21) Appl. No.: 18/023,767

(22) PCT Filed: Sep. 2, 2021

(86) PCT No.: PCT/US2021/048777
§ 371 (c)(1),
(2) Date: Feb. 28, 2023

(87) PCT Pub. No.: WO2022/051442
PCT Pub. Date: Mar. 10, 2022

(65) Prior Publication Data

US 2023/0357167 A1 Nov. 9, 2023

Related U.S. Application Data

(60) Provisional application No. 63/074,024, filed on Sep. 3, 2020.

(51) Int. Cl.
*C07D 243/24* (2006.01)
*A61K 31/5513* (2006.01)

(52) U.S. Cl.
CPC ........ *C07D 243/24* (2013.01); *A61K 31/5513* (2013.01); *C07B 2200/13* (2013.01)

(58) Field of Classification Search
CPC ............ A61K 31/5513; C07B 2200/13; C07D 243/24
See application file for complete search history.

(56) References Cited

U.S. PATENT DOCUMENTS

| | | | | |
|---|---|---|---|---|
| 8,629,136 | B2 | 1/2014 | Gavai et al. | |
| 9,273,014 | B2 | 3/2016 | Gavai et al. | |
| 2014/0087992 | A1* | 3/2014 | Gavai | C07D 243/18 540/487 |
| 2014/0100365 | A1 | 4/2014 | Gavai et al. | |
| 2015/0231152 | A1 | 8/2015 | Zhao et al. | |
| 2020/0055948 | A1 | 2/2020 | Daley et al. | |

FOREIGN PATENT DOCUMENTS

| | | | |
|---|---|---|---|
| CN | 105439939 | A | 3/2016 |
| JP | 2015530411 | A | 10/2015 |
| WO | 2014047372 | A1 | 3/2014 |
| WO | 2022051442 | A1 | 3/2022 |

OTHER PUBLICATIONS

Aung, K. L. et al. (2018). A multi-arm phase I dose escalating study of an oral NOTCH inhibitor BMS-986115 in patients with advanced solid tumours. *Investigational New Drugs*, 36, 1026-1036.
International Search Report and Written Opinion of the International Searching Authority dated Dec. 16, 2021, issued in the corresponding PCT International Application No. PCT/US2021/048777, dated Sep. 2, 2021.
Ashizawa, K., "Science of Polymorphism and Crystallization of Pharmaceuticals," Maruzen Planet Co., Ltd., 2002.
Caira, M., "Crystalline Polymorphism of Organic Compounds," Topics in Current Chemistry, Springer, Berlin, DE, vol. 198(1):163-208, Jan. 1998 (Jan. 1, 1998).
Hirayama, N., Handbook of Organic Compound Crystal Fabrication, Maruzen Co., Ltd., 2008, pp. 3. CN-A 105439939.

* cited by examiner

*Primary Examiner* — Theodore R. Howell
(74) *Attorney, Agent, or Firm* — Antheros Legal Advisors LLP

(57) ABSTRACT

The present invention provides a crystalline form of (2R, 3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinimide, represented by the structure of Compound (1), wherein the crystalline form comprises N-2 crystalline form, IPA2-1 crystalline form, M3-1 crystalline form, P4 crystalline form, P5 crystalline form, P6 crystalline form, or any combination thereof. The present invention also provides processes for the preparation of a the crystalline form, and pharmaceutical compositions comprising one or more of the crystalline forms.

(1)

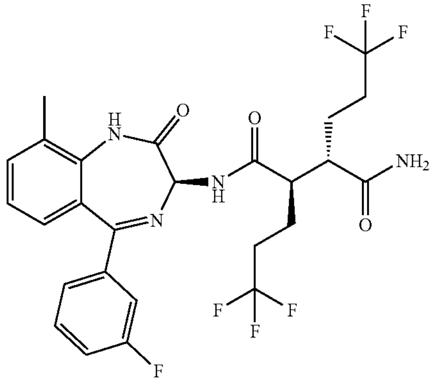

35 Claims, 18 Drawing Sheets

POLYMORPHS OF BIS(FLUOROALKYL)-1,4-BENZODIAZEPINONE COMPOUNDS AND USES THEREOF

CROSS-REFERENCE TO RELATED APPLICATIONS

This application is a National Phase Application of PCT International Application No. PCT/US2021/048777, International Filing Date Sep. 2, 2021, claiming the benefit of U.S. Patent Application No. 63/074,024, filed Sep. 3, 2020, which are hereby incorporated by reference.

FIELD OF THE INVENTION

The present invention provides a crystalline form of (2R,3S)—N-((3S)-5-(3-fluorophenyl)-9-methyl-2-oxo-2,3-dihydro-1H-1,4-benzodiazepin-3-yl)-2,3- bis(3,3,3-trifluoropropyl)succinimide, represented by the structure of Compound 1:

(1)

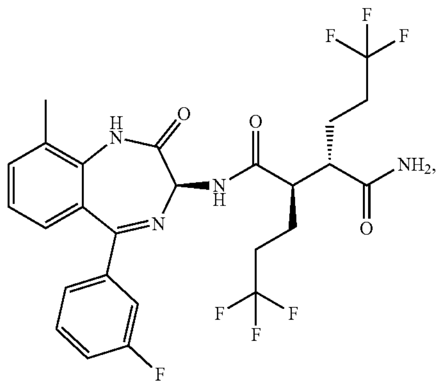

processes of preparation, compositions and uses thereof.

BACKGROUND OF THE INVENTION

Benzodiazepinone compounds are useful as pharmaceutically active ingredients in the pharmaceutical and fine chemical industries. For example, the gamma-secretase inhibitor (GSI) (2R,3S)—N1-[(3S)-2,3-Dihydro-1-methyl-2-oxo-5-phenyl-1H-1,4-benzodiazepin-3-yl]-2,3-bis(3,3,3-trifluoropropyl)-butanediamide:

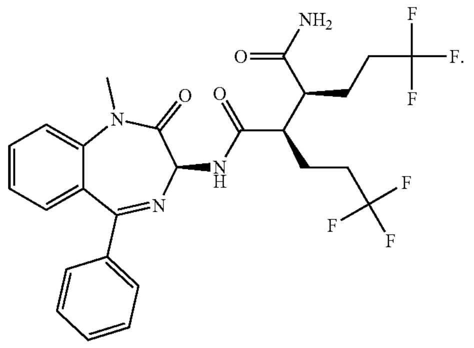 [SMILES: CN1C(=O)[C@@H](NC(=O)[C@H](CCC(F)(F)F)[C@H](CCC(F)(F)F)C(N)=O)N=C(c2ccccc2)c2ccccc21]

is showing promising results in current clinical trials for the treatment of various cancers (see U.S. Pat. No. 8,629,136, incorporated herein by reference). Crystalline forms of pharmaceutically active agents, such as those disclosed in U.S. Pat. No. 8,629,136, that possess desirable physiochemical properties, such as high bioavailability, solubility, melting point, and crystallinity, were identified.

U.S. Pat. No. 9,273,014, incorporated herein by reference, describes the preparation of Compound 1 and some of its uses. However, crystalline structures of Compound 1 were not disclosed. Crystalline forms of Compound 1 having desirable physiochemical properties are therefore needed to provide forms of Compound 1 with high bioavailability, solubility, melting point, and crystallinity.

SUMMARY OF THE INVENTION

In one embodiment, the present invention provides a crystalline form of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinimide, represented by the structure of Compound 1:

(1)

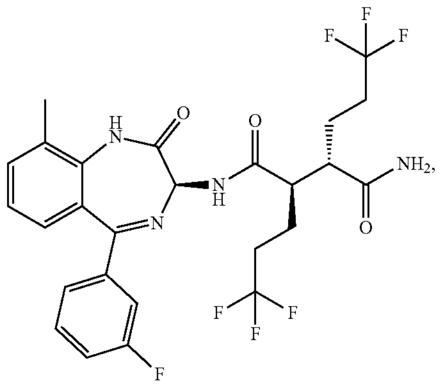

wherein the crystalline form comprises N-2 crystalline form, IPA2-1 crystalline form, M3-1 crystalline form, P4 crystalline form, P5 crystalline form, P6 crystalline form, or any combination thereof.

In another embodiment, the present invention provides a crystalline form of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinimide, represented below:

(1)

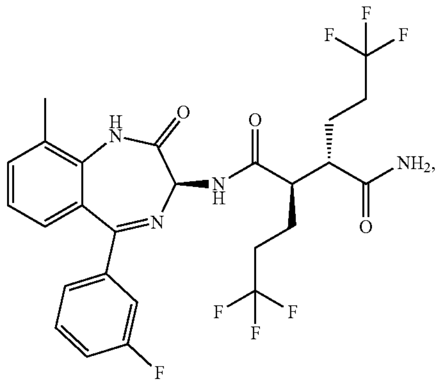

wherein the crystalline form comprises a P1 crystalline form; and the P1 crystalline form is crystallized via desolvation of crystalline form IPA2-1 or M3-1, wherein IPA2-1 and M3-1 are additional crystalline forms of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinimide.

In another embodiment, the present invention provides a crystalline form of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinimide, represented below:

(1)

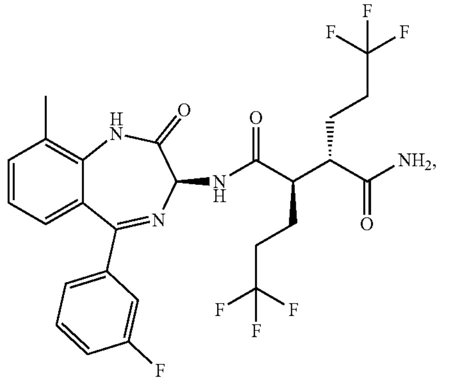

wherein the crystalline form comprises a P2 crystalline form; and the P2 crystalline form is crystallized from crystalline form P1 as described above and which was slurried in ethyl acetate.

In another embodiment, the present invention provides a crystalline form of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinimide, represented below:

(1)

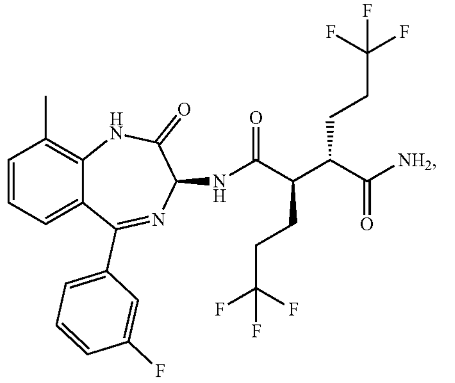

wherein the crystalline form comprises a P3 crystalline form; and the P3 crystalline form is crystallized from crystalline form P1 as described above and which was slurried in acetonitrile.

In another embodiment, the present invention provides a pharmaceutical composition comprising a therapeutically effective amount of the crystalline form as described above and a pharmaceutically acceptable carrier.

DETAILED DESCRIPTION

In the following detailed description, numerous specific details are set forth in order to provide a thorough understanding of the present invention. However, it will be understood by those skilled in the art that the present invention may be practiced without these specific details. In other instances, well-known methods, procedures, and components have not been described in detail so as not to obscure the present invention.

Crystalline Forms of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinimide (Compound 1)

In one embodiment, the present invention provides a crystalline form of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinimide (Compound 1), represented by the structure of Compound 1:

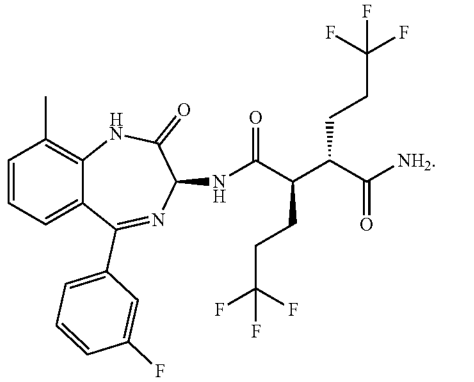

(1)

In one embodiment, the crystalline form comprises the N-2 crystalline form, the IPA2-1 crystalline form, the M3-1 crystalline form, the E2-1 crystalline form, the P1 crystalline form, the P2 crystalline form, the P3 crystalline form, the P4 crystalline form, the P5 crystalline form, the P6 crystalline form, or any combination thereof. In another embodiment, the crystalline form comprises the N-2 crystalline form, the IPA2-1 crystalline form, the M3-1 crystalline form, the P4 crystalline form, the P5 crystalline form, the P6 crystalline form, or any combination thereof. In yet another embodiment, the crystalline form comprises the E2-1 crystalline form, the P1 crystalline form, the P2 crystalline form, the P3 crystalline or any combination thereof. Each possibility represents a separate embodiment of the present invention.

In another embodiment, the present invention provides a crystalline form of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinimide (Compound 1), represented by the structure of Compound 1:

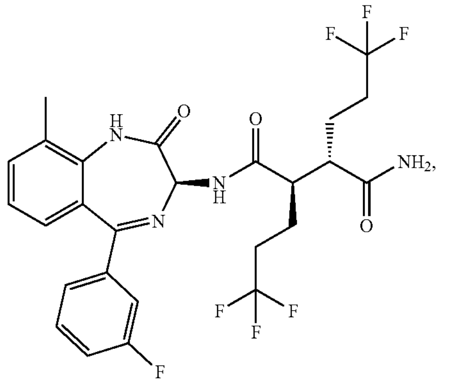

(1)

wherein the crystalline form comprises the N-2 crystalline form.

Figure 1:
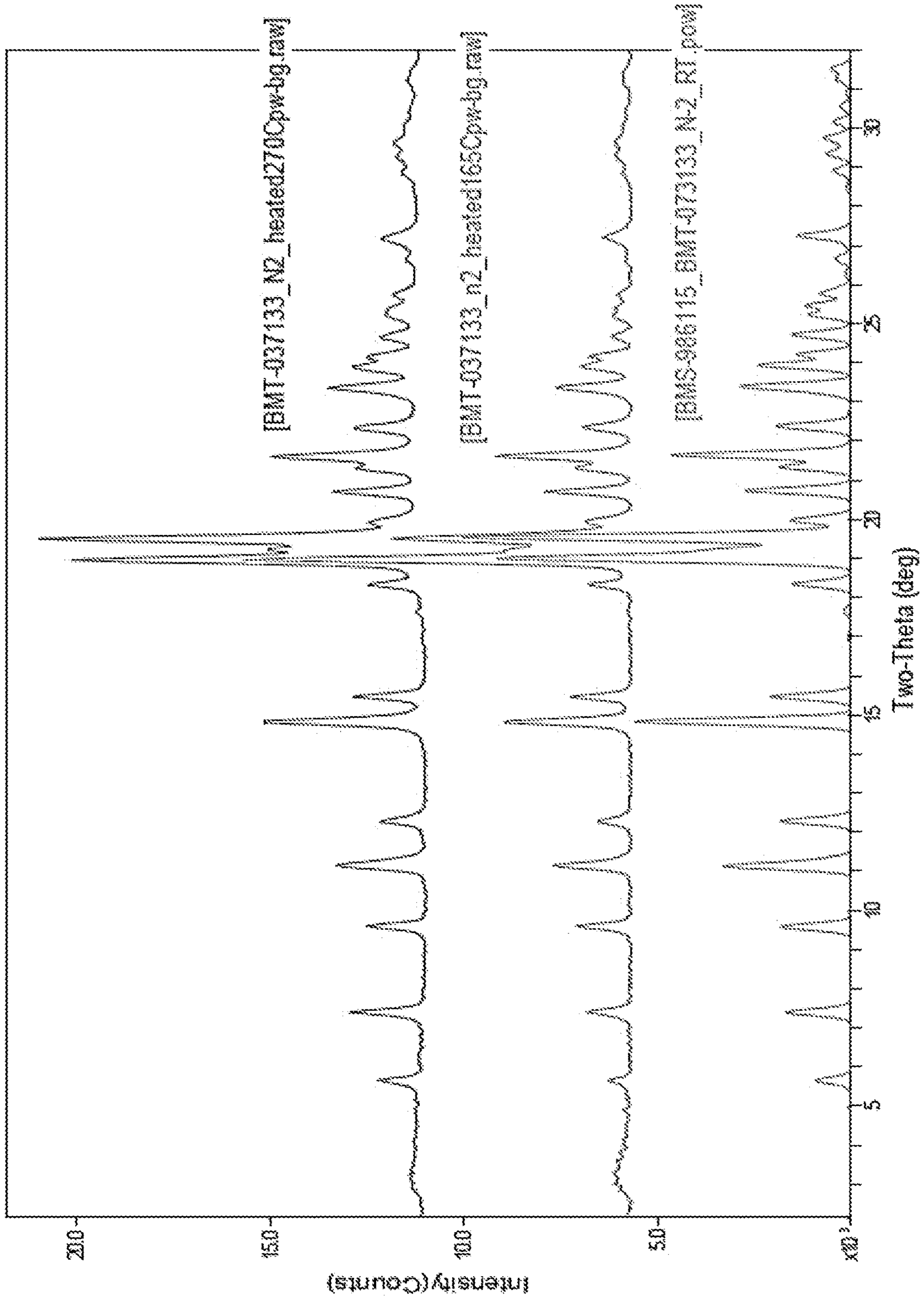
FIG. 1 depicts PXRD patterns of the N-2 form at room temperature (bottom), 165° C. (middle) and 270° C. (top).

In one embodiment, the N-2 crystalline form is crystallized from ethanol/water. In another embodiment, the crystalline form N-2 is characterized by an XRPD pattern having peaks at 14.92±0.3, 15.49±0.3, 19.3±0.3, 19.64±0.3 and 21.57±0.3 degrees two theta (2θ); or characterized by unit cell parameters of a=4.84±0.3 Å, b=18.47±0.3 Å, c=15.67±0.3 Å, a=90°, b=91.62±0.5°, g=90°, unit cell volume is 1399.51±0.5 $Å^3$, number of compound per asymmetric unit is 1 and space group is $P2_1$. In another embodiment, the XRPD pattern of the crystalline form N-2 has additional peaks at 11.12±0.3 and 12.23±0.3 degrees two theta (2θ). In another embodiment, the crystalline form N-2 is characterized by an XRPD pattern substantially as represented by FIG. 1. Each possibility represents a separate embodiment of the present invention.

Figure 2:
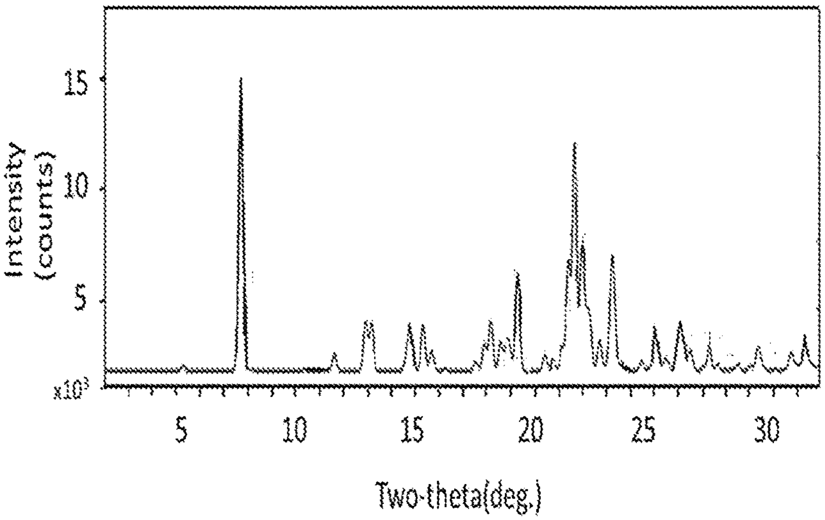
FIG. 2 depicts the PXRD pattern of the IPA2-1 form.

In another embodiment, the present invention provides a crystalline form of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinimide (Compound 1), represented by the structure of Compound 1:

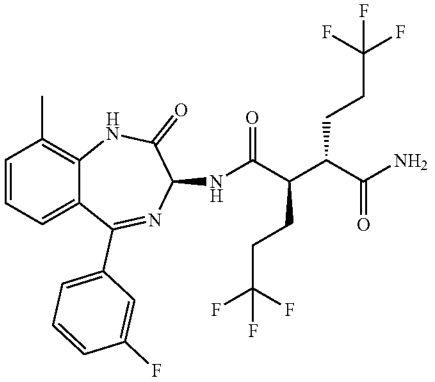 [SMILES: Cc1cccc2c1NC(=O)[C@@H](NC(=O)[C@H](CCC(F)(F)F)[C@H](CCC(F)(F)F)C(N)=O)N=C2c1cccc(F)c1]

wherein the crystalline form comprises the IPA2-1 crystalline form. In one embodiment, the IPA2-1 crystalline form is crystallized from isopropyl alcohol (IPA). In another embodiment, the crystalline form IPA2-1 is characterized by an XRPD pattern having peaks at 7.71±0.3, 12.96±0.3, 13.12±0.3, 14.84±0.3 and 19.35±0.3 degrees two theta (2θ); or characterized by unit cell parameters of a=11.93±0.3 Å, b=8.57±0.3 Å, c=17.42±0.3 Å, a=90°, b=105.16±0.5°, g=90°, unit cell volume is 1718.67±0.5 $Å^3$, number of compound per asymmetric unit is 1 and space group is $P2_1$. In another embodiment, the XRPD pattern of the IPA2-1 crystalline form has additional peaks at 21.62±0.3 and 21.83±0.3 degrees two theta (2θ). In another embodiment, the crystalline form IPA2-1 is characterized by an XRPD pattern substantially as represented by FIG. 2. Each possibility represents a separate embodiment of the present invention.

In another embodiment, the present invention provides a crystalline form of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinimide (Compound 1), represented by the structure of Compound 1:

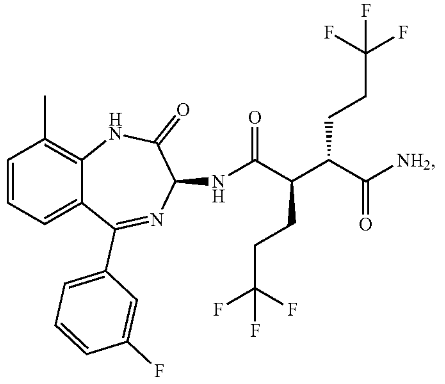

Figure 3:
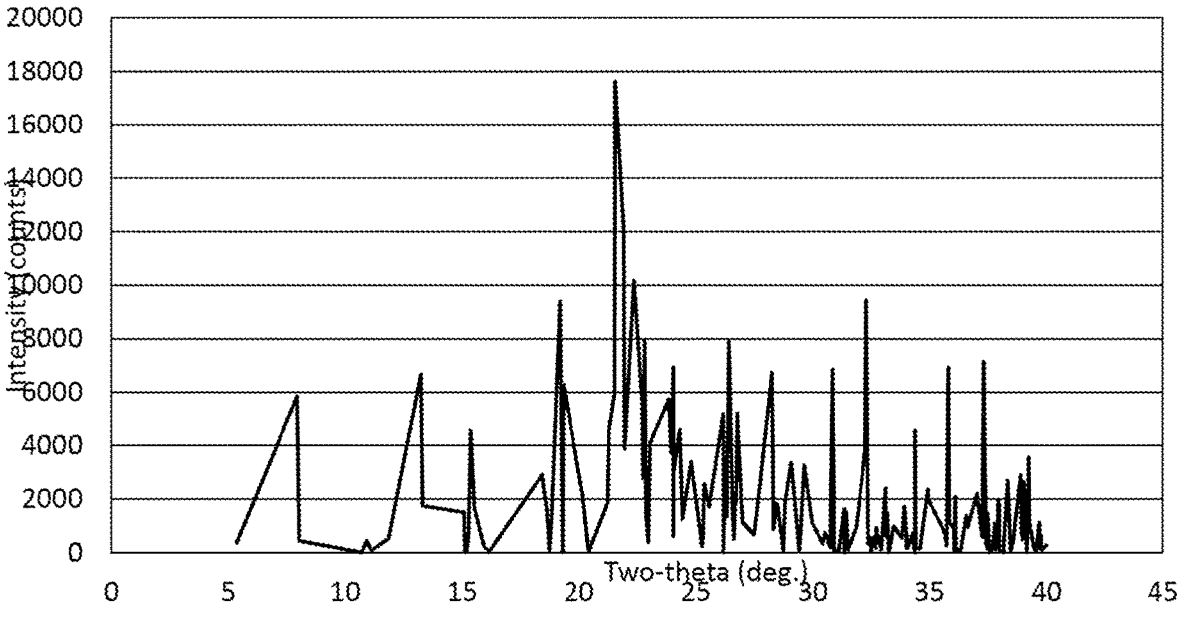
FIG. 3 depicts the PXRD pattern of the M3-1 form.

(1)

wherein the crystalline form comprises the M3-1 crystalline form. In one embodiment, the M3-1 crystalline form is crystallized from methanol. In another embodiment, the crystalline form M3-1 is characterized by an XRPD pattern having peaks at 7.96±0.3, 13.26±0.3, 19.19±0.3 and 21.56±0.3 degrees two theta (2θ); or characterized by unit cell parameters of a=11.72±0.3 Å, b=8.36±0.3 Å, c=17.41±0.3 Å, a=90°, b=108.62±0.5°, g=90°, unit cell volume is 1616.59±0.5 $Å^3$, number of compound per asymmetric unit is 1 and space group is $P2_1$. In another embodiment, the crystalline form M3-1 is characterized by an XRPD pattern substantially as represented by FIG. 3. Each possibility represents a separate embodiment of the present invention.

In another embodiment, the present invention provides a crystalline form of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinimide (Compound 1), represented by the structure of Compound 1:

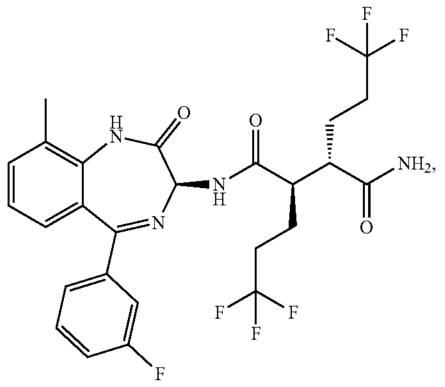

Figure 4:
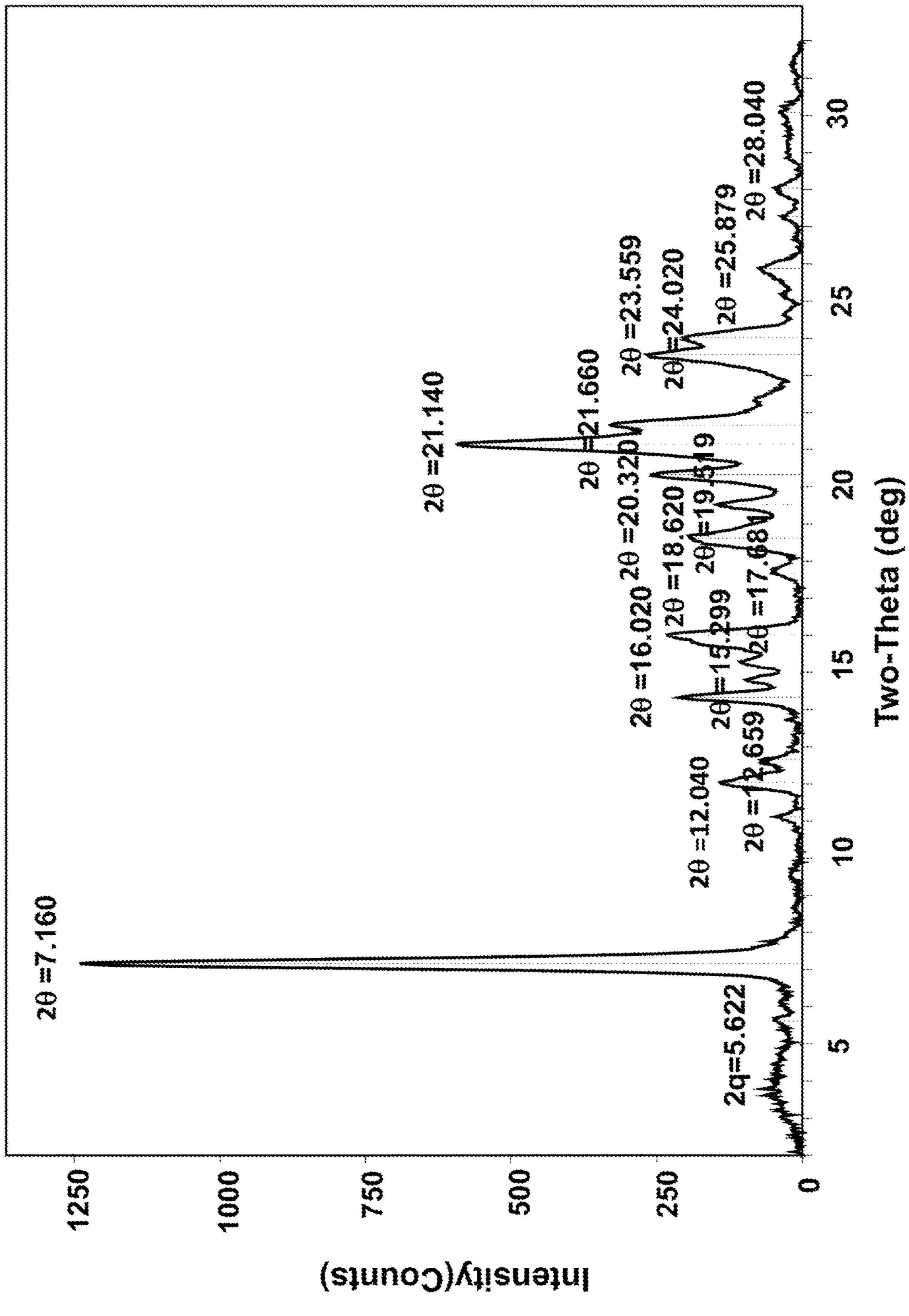
FIG. 4 depicts the PXRD pattern of the P4 form.

(1)

wherein the crystalline form comprises the P4 crystalline form. In one embodiment, the P4 crystalline form is crystallized from v/v 1:1 MeCN/MTBE, 1:2 DCM/Heptane, 1:1 DCM/MTBE or 1:1 MEK/Cyclohexane. In another embodiment, the crystalline form P4 is characterized by an XRPD pattern having peaks at 7.16±0.3, 16.02±0.3, 18.62±0.3, 20.32±0.3 and 21.14±0.3 degrees two theta (2θ). In another embodiment, the XRPD pattern of the P4 crystalline form has additional peaks at 12.04±0.3 and 23.56±0.3 degrees two theta (2θ). In another embodiment, the crystalline form P4 is characterized by an XRPD pattern substantially as represented by FIG. 4. Each possibility represents a separate embodiment of the present invention.

In another embodiment, the present invention provides a crystalline form of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinimide (Compound 1), represented by the structure of Compound 1:

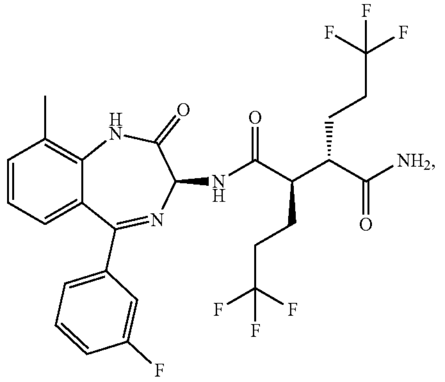

Figure 5:
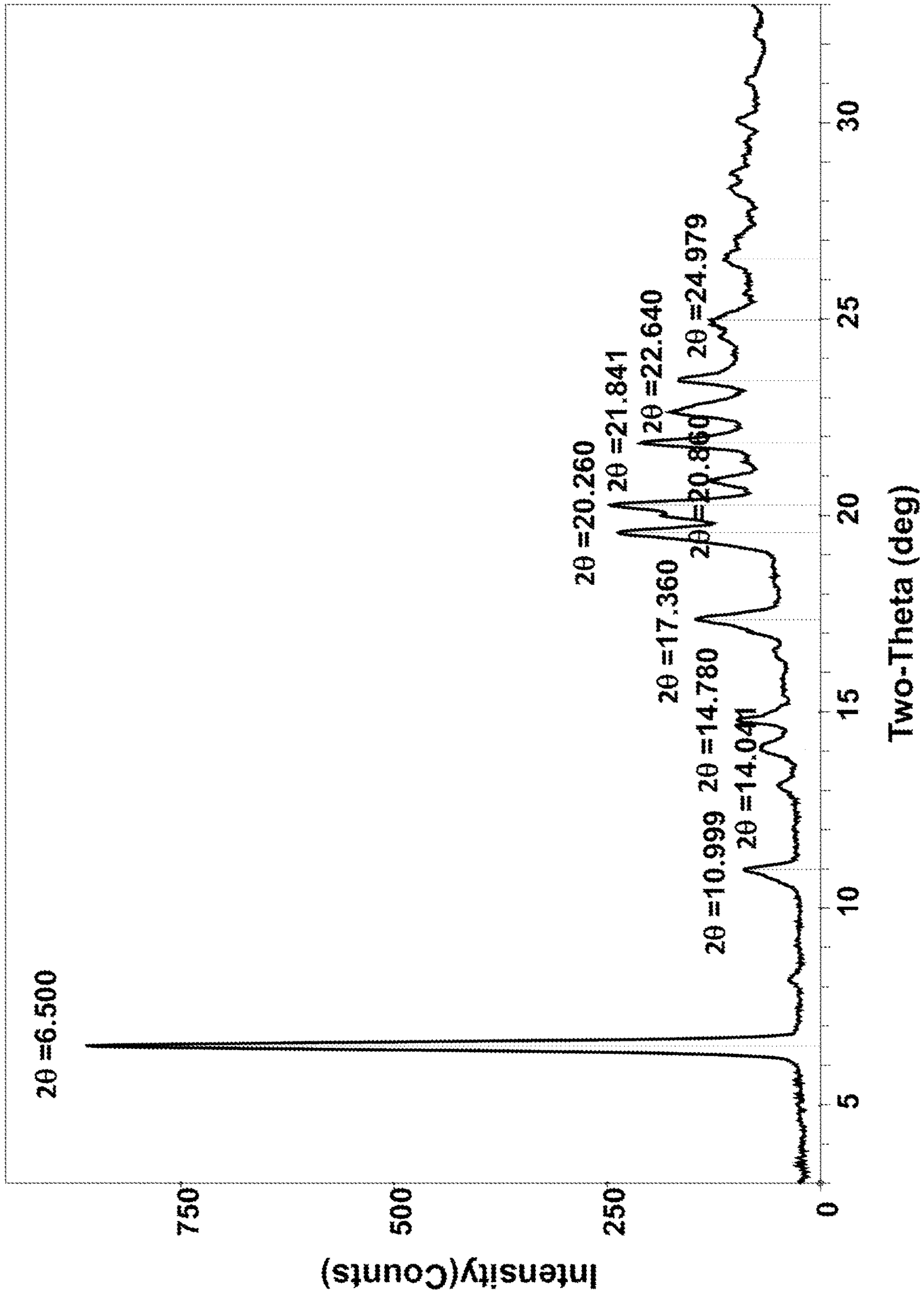
FIG. 5 depicts the PXRD pattern of the P5 form.

(1)

wherein the crystalline form comprises the P5 crystalline form. In one embodiment, the P5 crystalline form is crystallized from acetone:water 1:1 v/v. In another embodiment, the crystalline form P5 is characterized by an XRPD pattern having peaks at 6.5±0.3, 10.99±0.3, 17.36±0.3, 19.49±0.3 and 21.84±0.3 degrees two theta (2θ). In another embodiment, the XRPD pattern of the P5 crystalline form has additional peaks at 14.78±0.3 and 20.26±0.3 degrees two theta (2θ). In another embodiment, the crystalline form P5 is characterized by an XRPD pattern substantially as represented by FIG. 5. Each possibility represents a separate embodiment of the present invention.

In another embodiment, the present invention provides a crystalline form of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinimide (Compound 1), represented by the structure of Compound 1:

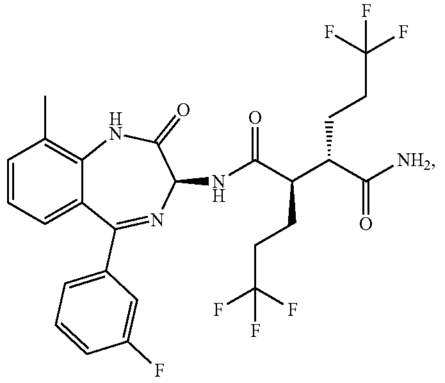

Figure 6:
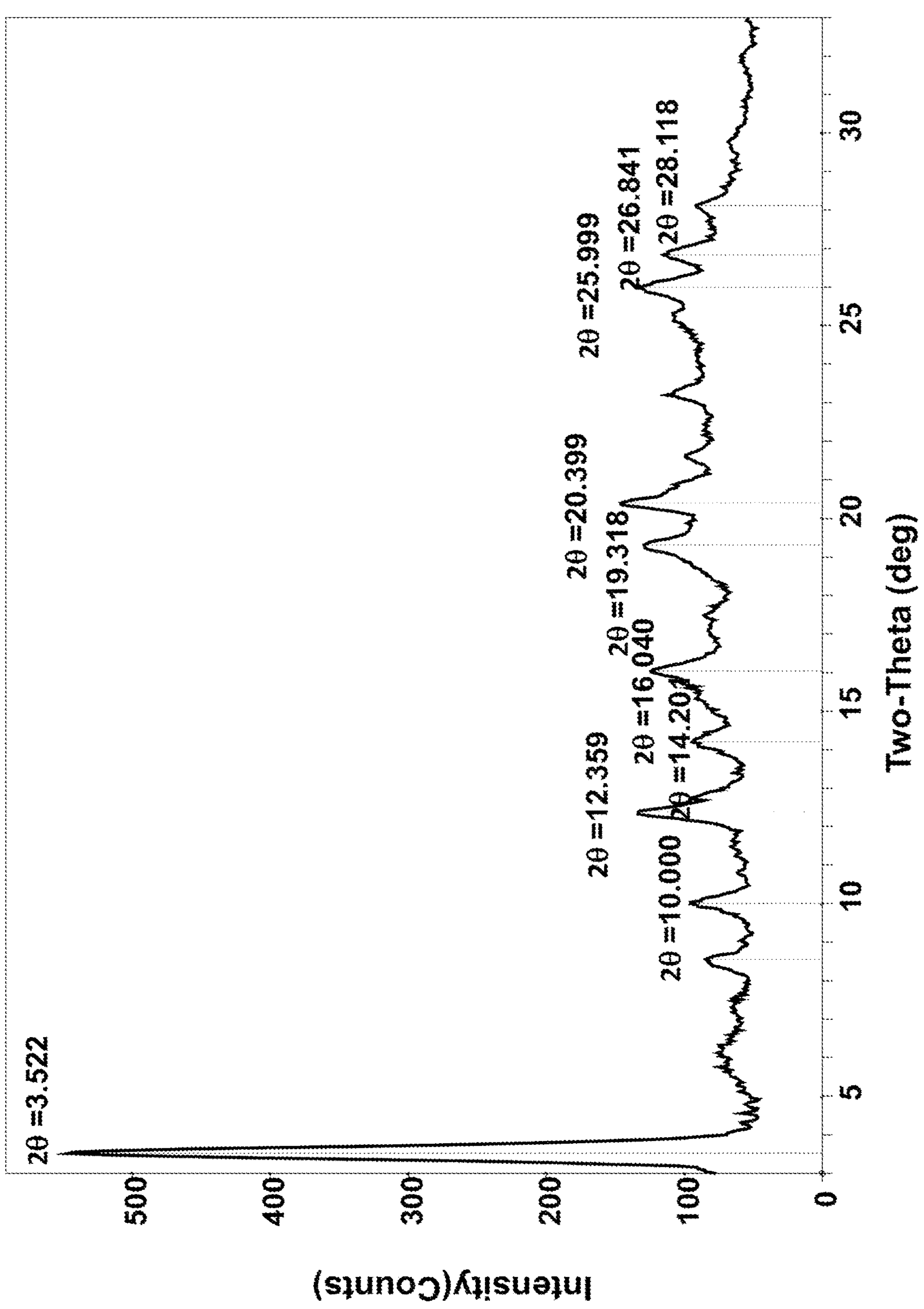
FIG. 6 depicts the PXRD pattern of the P6 form.

(1)

wherein the crystalline form comprises the P6 crystalline form. In one embodiment, the P6 crystalline form is crystallized from ethanol:water 1:1 v/v. In another embodiment, the crystalline form P6 is characterized by an XRPD pattern having peaks at 3.52±0.3, 10.00±0.3, 12.36±0.3, 19.32±0.3 and 20.40±0.3 degrees two theta (2θ). In another embodiment, the XRPD pattern of the crystalline form P6 has additional peaks at 14.2±0.3 and 16.04±0.3 degrees two theta (20). In another embodiment, the crystalline form P6 is characterized by an XRPD pattern substantially as represented by FIG. 6. Each possibility represents a separate embodiment of the present invention.

In another embodiment, the present invention provides a crystalline form of (2R,3S)—N-((3S)-5-(3-fluorophenyl)-9- methyl-2-oxo-2,3-dihydro-1H-1,4-benzodiazepin-3-yl)-2,3-bis(3,3,3-trifluoropropyl)succinimide (Compound 1), represented by the structure of Compound 1:

(1)

Figure 7:
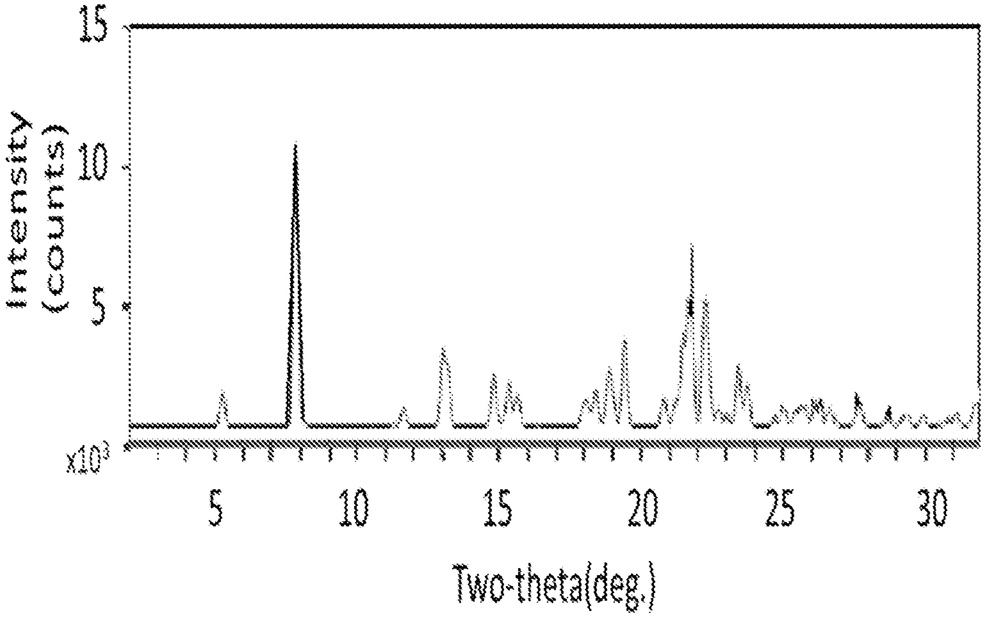
FIG. 7 depicts the PXRD pattern of the E2-1 form.

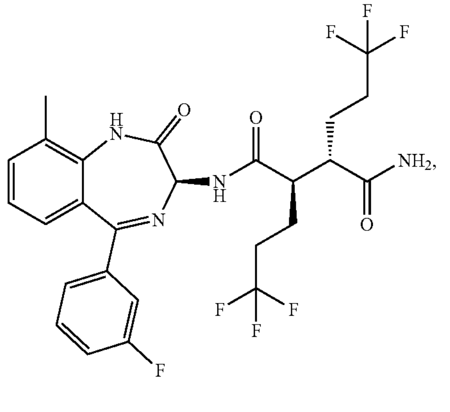

wherein the crystalline form comprises the E2-1 crystalline form. In one embodiment, the E2-1 crystalline form is crystallized from THF/heptane. In another embodiment, the E2-1 crystalline form is crystallized from acetone/heptanes. In another embodiment, the E2-1 crystalline form is crystallized from propylene glycol. In another embodiment, the E2-1 crystalline form is crystallized from ethanol/water. Each possibility represents a separate embodiment of the present invention. In another embodiment, the E2-1 crystalline form is crystallized from THF/heptane, acetone/heptanes, or propylene glycol. In one embodiment, the crystalline form E2-1 is characterized by an XRPD pattern having peaks at 37.87±0.3, 13.09±0.3, 18.88±0.3, 19.41±0.3 and 21.62±0.3 degrees two theta (2q); or characterized by unit cell parameters of a=11.70±0.3 Å, b=8.53±0.3 Å, c=17.42±0.3 Å, α=90°, β=106.03±0.5°, γ=90°, unit cell volume is 1672.01±0.5 $Å^3$, number of compound per asymmetric unit is 1 and space group is $P2_1$. In another embodiment, the XRPD pattern of the crystalline form E2-1 has additional peaks at 21.83±0.3 and 22.3±0.3 degrees two theta (2θ). In another embodiment, the crystalline form E2-1 is characterized by an XRPD pattern substantially as represented by FIG. 7. Each possibility represents a separate embodiment of the present invention.

In another embodiment, the present invention provides a crystalline form of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinimide (Compound 1), represented by the structure of Compound 1:

(1)

Figure 8:
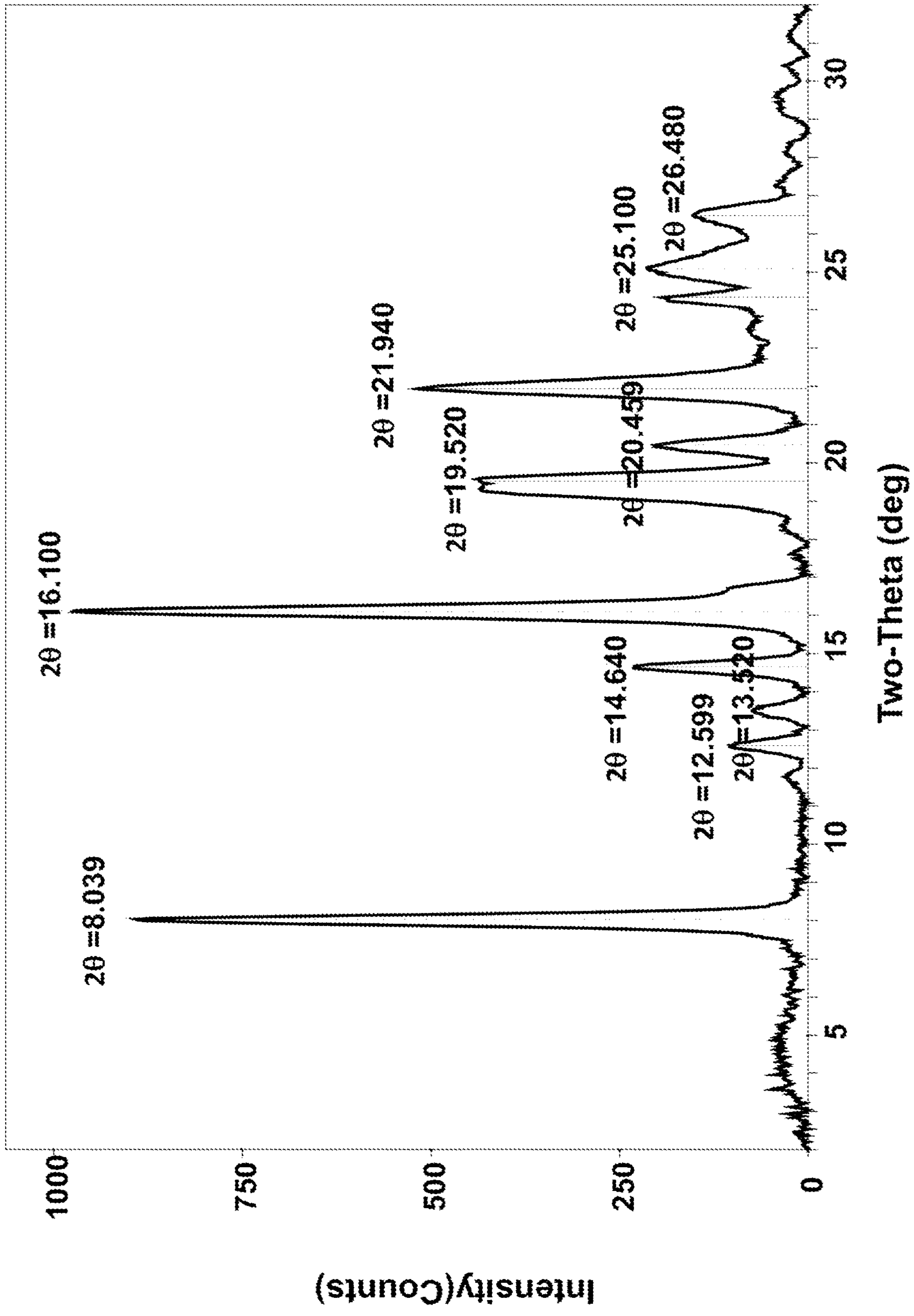
FIG. 8 depicts the PXRD pattern of the P1 form.

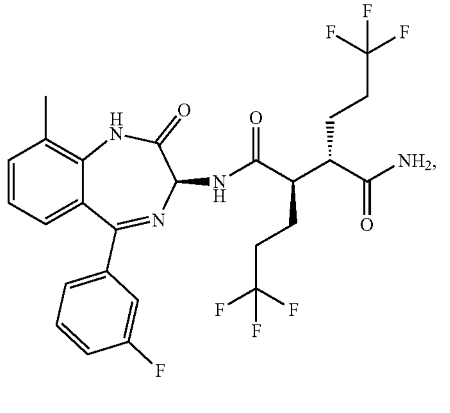

wherein the crystalline form comprises the P1 crystalline form. In one embodiment, the P1 crystalline form is crystallized via desolvation of crystalline form E2-1. In another embodiment, the P1 crystalline form is crystallized via desolvation of IPA2-1. In another embodiment, the P1 crystalline form is crystallized via desolvation of M3-1. Each possibility represents a separate embodiment of the present invention. In one embodiment, the crystalline form P1 is characterized by an XRPD pattern having peaks at 8.04±0.3, 14.64±0.3, 16.1±0.3, 19.52±0.3 and 21.94±0.3 degrees two theta (2θ). In another embodiment, the XRPD pattern of the crystalline form P1 has additional peaks at 20.46±0.3 and 25.1±0.3 degrees two theta (2θ). In another embodiment, the crystalline form P1 is characterized by an XRPD pattern substantially as represented by FIG. 8. Each possibility represents a separate embodiment of the present invention.

In another embodiment, the present invention provides a crystalline form of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinimide (Compound 1), represented by the structure of Compound 1:

(1)

Figure 9:
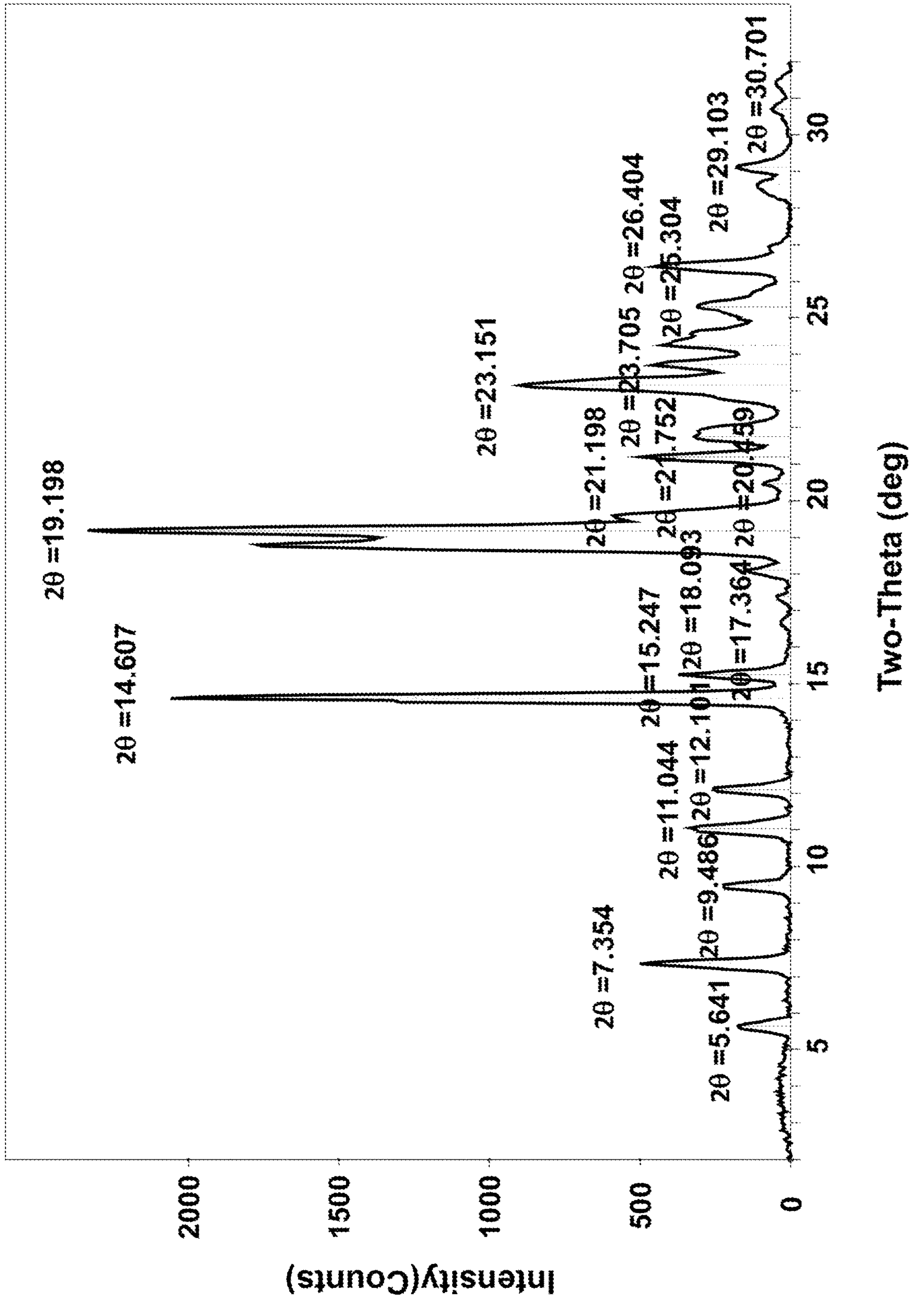
FIG. 9 depicts the PXRD pattern of the P2 form.

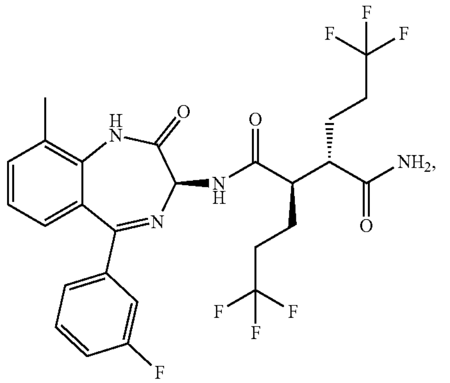

wherein the crystalline form comprises the P2 crystalline form. In one embodiment, the P2 crystalline form is crystallized from crystalline form P1 as described hereinabove, which was slurried in ethyl acetate. In one embodiment, the crystalline form P2 is characterized by an XRPD pattern having peaks at 7.35±0.3, 14.61±0.3, 19.2±0.3, 23.15±0.3 and 26.4±0.3 degrees two theta (2θ). In another embodiment, the XRPD pattern of the crystalline form P2 has additional peaks at 11.04±0.3 and 23.71±0.3 degrees two theta (2θ). In another embodiment, the crystalline form P2 is characterized by an XRPD pattern substantially as represented by FIG. 9. Each possibility represents a separate embodiment of the present invention.

In another embodiment, the present invention provides a crystalline form of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinimide (Compound 1), represented by the structure of Compound 1:

(1)

Figure 10:
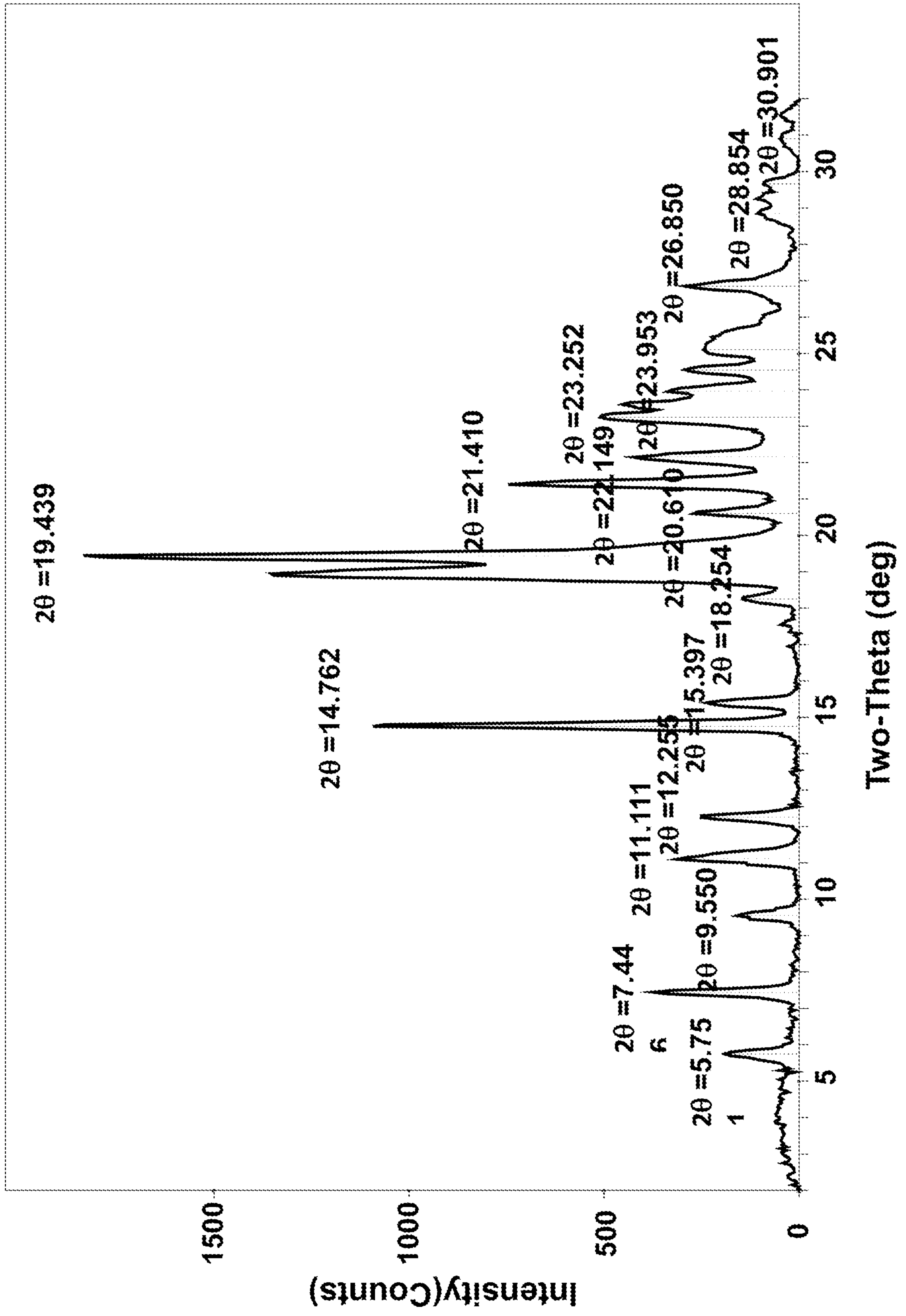
FIG. 10 depicts the PXRD pattern of the P3 form.

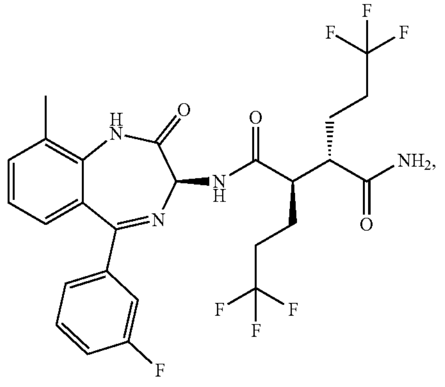

wherein the crystalline form comprises the P3 crystalline form. In one embodiment, the P3 crystalline form is crystallized from the P1 crystalline form slurried in ethyl acetate as described hereinabove. In one embodiment, the crystalline form P3 is characterized by an XRPD pattern having peaks at 87.45±0.3, 14.76±0.3, 19.02±0.3, 19.44±0.3 and 21.41±0.3 degrees two theta (2θ). In another embodiment, the XRPD pattern of the crystalline form P3 has additional peaks at 11.11±0.3 and 22.15±0.3 degrees two theta (2θ). In another embodiment, the crystalline form P3 is characterized by an XRPD pattern substantially as represented by FIG. 10. Each possibility represents a separate embodiment of the present invention.

In another embodiment, crystallization of a crystalline form which was formed in a specific solvent has a different crystal habit than the same crystalline form which was formed from a different solvent. In another embodiment, crystallization of a crystalline form which was formed in a specific solvent has a different particle size than the same crystalline form which was formed from a different solvent.

Processes of Preparing Crystalline Forms of (2R, 3S)—N-((3S)-5-(3-fluorophenyl)-9-methyl-2-oxo-2, 3-dihydro-1H-1,4-benzodiazepin-3-yl)-2,3-bis(3,3,3-trifluoropropyl)succinimide (Compound 1)

In one embodiment, the present invention provides a process of preparing the crystalline form of Compound 1 of the present invention, comprising:

Dissolving Compound 1 in a solvent;

Adding an anti-solvent to the solution, to afford a precipitate; and

Isolating the precipitate to provide a crystalline form of Compound 1.

In another embodiment, the present invention provides a process of preparing the crystalline form of Compound 1 of the present invention, comprising:

Heating and dissolving Compound 1 in a solvent;

Adding an anti-solvent to the heated solution;

Cooling the hot solution to afford a precipitate; and

Isolating the precipitate to provide a crystalline form of Compound 1.

In one embodiment, the present invention provides a process of preparing the crystalline form of Compound 1 of the present invention, comprising:

Mixing and dissolving Compound 1 in a solvent system to afford a precipitate; and Isolating the precipitate to provide a crystalline form of Compound 1.

In another embodiment, the present invention provides a process of preparing the crystalline form of Compound 1 of the present invention, comprising:

Mixing, heating and dissolving Compound 1 in a solvent system;

Cooling the hot solution to afford a precipitate; and

Isolating the precipitate to provide a crystalline form of Compound 1.

In another embodiment, the present invention provides a process of preparing the crystalline form of Compound 1 of the present invention, comprising:

Dissolving Compound 1 in a solvent in a flask;

Transferring the contents of the flask through a filter to obtain filtrate A;

Adding solvent to the flask;

Transferring the contents of the flask through a filter to obtain filtrate B;

Combining filtrates A and B in the flask, and adding an anti-solvent to provide a precipitate; and Drying the precipitate to provide a crystalline form of Compound 1.

In one embodiment, the solvent is acetic acid. In one embodiment, the anti-solvent is water. In one embodiment, the solvent is acetic acid and the anti-solvent is water. In one embodiment, the method further comprises adding the anti-solvent again to the dried precipitate, collecting the resulting wet precipitate ("cake"), filtering the wet precipitate, and drying the filtrate to obtain the crystalline form. In some embodiments, the latter step may be repeated one or more additional times, as needed (to obtain the highest possible purity). In some embodiments, the latter step may be repeating two, three, four, or five additional times.

In one embodiment, the N-2 crystalline form is prepared via dissolution of Compound 1 in acetic acid followed by addition of water which results in crystallization of Compound 1.

In some embodiments, non-limiting examples of solvents comprise MeOH, EtOH (including absolute EtOH), i-PrOH, i-PrOH/MeCN, n-BuOH, i-BuOH, i-BuOH/MeCN, acetone, MeCN, MEK (butanone), ethyl-formate, EtOAc, i-BuOAc, n-PrOAc, MeOAc, i-PrOAc, n-BuOAc, i-BuOAc, MIBK, anisole, n-PrOH, n-PrOH/MeCN, n-BuOH, n-BuOH/MeCN, s-BuOH, n-AmOH, DMSO/TBME, acetone/water, MeCN/water, EtOH/water, i-PrOH/water, n-PrOH/water, EtOH/n-PrOAc, i-PrOH/n-PrOAc, n-PrOH/n-PrOAc, n-PrOH/heptane, n-BuOH/heptane, water, Acetic acid, Formic acid and mixtures thereof. Each possibility represents a separate embodiment of the present invention.

In some embodiments, non-limiting examples of anti-solvents comprise water, EtOAc, acetone, acetonitrile and mixtures thereof. Each possibility represents a separate embodiment of the present invention.

In some embodiment, a solvent system comprises at least one solvent and/or anti-solvent as described hereinabove. In one embodiment, non-limiting examples of solvent systems comprise acetic acid/water, EtOH/water (e.g. 1:1, 1:2), EtOH, MeOH, IPA, THF/heptane, acetone/heptanes, propylene glycol, MeCN/MTBE (e.g. 1:1), DCM/heptane (e.g. 1:2), DCM/MTBE (e.g. 1:1) MEK/cyclohexane (e.g. 1:1), acetone/water (e.g. 1:1), IPA/water (e.g. 1:2, 1:1), THF/n-heptane (e.g. 1:1), THF/water (e.g. 1:1), acetone/n-heptane (e.g. 1:1), water, ethyl acetate, DCM, acetonitrile, acetonitrile/water (e.g. 1:1), acetic acid/water (e.g. 1:1) and DMSO/water (e.g. 1:1). Each possibility represents a separate embodiment of the present invention.

In some embodiments, the Compound 1+solvent/solvent system mixture is heated to the temperature of medium (solvent/solvent system) reflux. In one embodiment, the mixture is heated to a temperature of 40-150° C. In another embodiment, the mixture is heated to a temperature of 40-100° C. In another embodiment, the mixture is heated to a temperature of 40-80° C. In another embodiment, the mixture is heated to a temperature of 40-60° C. In another embodiment, the mixture is heated to a temperature of 60-80° C. In another embodiment, the mixture is heated to a temperature of 80-100° C. In another embodiment, the mixture is heated to a temperature of 100-120° C. In another embodiment, the mixture is heated to a temperature of 120-150° C. In another embodiment, the mixture is heated to a temperature of 80° C. In another embodiment the mixture is not heated. In another embodiment, the mixture is stirred at room temperature. Each possibility represents a separate embodiment of the present invention.

In some embodiments, precipitate isolation is performed using vacuum filtration, optionally accompanied with a solvent wash and/or via any other method known in the art.

In some embodiments, the mixture is cooled to a temperature of 10-30° C. In one embodiment, the mixture is cooled to a temperature of −50-25° C. In another embodiment, the mixture is cooled to a temperature of −20-0° C. In another embodiment, the mixture is cooled to a temperature of 0-25° C. In one embodiment, the mixture is cooled to a temperature of 0-10° C. Each possibility represents a separate embodiment of the present invention.

In some embodiments, heating and/or cooling is performed in one or more than one step(s).

Pharmaceutical Compositions Comprising Crystalline Forms of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinimide (Compound 1)

In one embodiment, the present invention provides a pharmaceutical composition comprising a therapeutically effective amount of a crystalline form of Compound 1 as described hereinabove and optionally at least one pharmaceutically acceptable carrier, diluent, vehicle or excipient. In one embodiment, the form of the pharmaceutical composition comprises sterile injectable solutions. In another embodiment, the form of the pharmaceutical composition comprises tablets (including e.g. film-coated tablets), powders, granules, capsules (including soft capsules), orally disintegrating tablets, pills, pellets, lozenges, sachets, cachets, patches, elixirs, suspensions, dispersions, emulsions, solutions, syrups, aerosols, ointments, soft and hard gelatin capsules, suppositories, sterile packaged powders, and sustained-release preparations, as are well known in the art. In another embodiment, the composition is a solid state composition (e.g. tablet, pill, capsule, pellet, granule, powder etc.). Each possibility represents a separate embodiment of the present invention.

In some embodiment, pharmacologically acceptable carriers, diluents, vehicles or excipients that may be used in the context of the present invention include, but are not limited to, surfactants, lubricants, binders, fillers, compression aids, disintegrants, water-soluble polymers, inorganic salts, preservatives, antioxidants, coloring agents, sweetening agents, souring agents, bubbling agents and flavorings. Each possibility represents a separate embodiment of the present invention.

In some embodiments, specific non-limiting examples of suitable carriers, diluents, vehicles or excipients within the present invention include e.g. lactose, D-mannitol, starch, cornstarch, crystalline cellulose, light silicic anhydride and titanium oxide. Each possibility represents a separate embodiment of the present invention. Suitable surfactants include e.g. lecithin and phosphatidylcholine. Each possibility represents a separate embodiment of the present invention. Suitable lubricants include e.g. magnesium stearate, sucrose fatty acid esters, polyethylene glycol, talc and stearic acid. Each possibility represents a separate embodiment of the present invention. Suitable binders include e.g. hydroxypropyl cellulose, hydroxypropylmethyl cellulose, crystalline cellulose, a-starch, polyvinylpyrrolidone, gum arabic powder, gelatin, pullulan and low-substitutional hydroxypropyl cellulose. Each possibility represents a separate embodiment of the present invention. Suitable disintegrants include e.g. crosslinked povidone (any crosslinked 1-ethenyl-2-pyrrolidinone homopolymer including polyvinylpyrrolidone (PVPP) and 1-vinyl-2-pyrrolidinone homopolymer), crosslinked carmellose sodium, carmellose calcium, carboxymethyl starch sodium, low-substituted hydroxypropyl cellulose, cornstarch and the like. Each possibility represents a separate embodiment of the present invention. Suitable water-soluble polymers include e.g. cellulose derivatives such as hydroxypropyl cellulose, polyvinylpyrrolidone, hydroxypropylmethyl cellulose, methyl cellulose and carboxymethyl cellulose sodium, sodium polyacrylate, polyvinyl alcohol, sodium alginate, guar gum, and the like. Each possibility represents a separate embodiment of the present invention. Suitable inorganic salts include e.g. basic inorganic salts of sodium, potassium, magnesium and/or calcium. Each possibility represents a separate embodiment of the present invention. Particular embodiments include the basic inorganic salts of magnesium and/or calcium. Basic inorganic salts of sodium include, for example, sodium carbonate, sodium hydrogen carbonate, disodiumhydrogenphosphate, and the like. Each possibility represents a separate embodiment of the present invention. Basic inorganic salts of potassium include, for example, potassium carbonate, potassium hydrogen carbonate, and the like. Each possibility represents a separate embodiment of the present invention. Basic inorganic salts of magnesium include, for example, heavy magnesium carbonate, magnesium carbonate, magnesium oxide, magnesium hydroxide, magnesium metasilicate aluminate, magnesium silicate, magnesium aluminate, synthetic hydrotalcite, aluminahydroxidemagnesium, and the like. Each possibility represents a separate embodiment of the present invention. Basic inorganic salts of calcium include, for example, precipitated calcium carbonate, calcium hydroxide, and the like. Each possibility represents a separate embodiment of the present invention.

Suitable preservatives include e.g. sodium benzoate, benzoic acid, and sorbic acid. Each possibility represents a separate embodiment of the present invention. Suitable antioxidants include e.g. sulfites, ascorbic acid and α-tocopherol. Each possibility represents a separate embodiment of the present invention. Suitable coloring agents include e.g. food colors such as Food Color Yellow No. 5, Food Color Red No. 2 and Food Color Blue No. 2, and the like. Each possibility represents a separate embodiment of the present invention. Suitable sweetening agents include e.g. dipotassium glycyrrhetinate, aspartame, stevia and thaumatin. Each possibility represents a separate embodiment of the present invention. Suitable souring agents include e.g. citric acid (citric anhydride), tartaric acid and malic acid. Each possibility represents a separate embodiment of the present invention. Suitable bubbling agents include e.g. sodium bicarbonate. Suitable flavorings include synthetic substances or naturally occurring substances, including e.g. lemon, lime, orange, menthol and strawberry. Each possibility represents a separate embodiment of the present invention.

In one embodiment, the present invention provides a pharmaceutical composition comprising a therapeutically effective amount of crystalline form of Compound 1 as described hereinabove and a pharmaceutically acceptable carrier. In another embodiment, the composition is in a solid state, suspension or emulsion form. In another embodiment, the composition is in a solid-state form; and the composition is a tablet. In a further embodiment, the composition is a suspension. In one embodiment, the suspension comprises the crystalline form and propylene glycol, which, in one embodiment, comprises solid crystals that are suspended in the solvent.

In one embodiment, the crystalline forms of the present invention are useful as pharmaceuticals for medical treatment. In one embodiment, the present invention thus provides pharmaceutical compositions comprising the crystalline form of Compound 1 disclosed herein and at least one pharmaceutically acceptable carrier, diluent, vehicle or excipient. The crystalline forms of the present invention may be safely administered orally or non-orally. In one embodiment, the route of administration comprises the intravenous route. Routes of administration also include, but are not limited to, oral, topical, subcutaneous, intraperitoneal, rectal, intravenous, intra-arterial, transdermal, intramuscular, topical, and intranasal. Each possibility represents a separate embodiment of the present invention. Additional routes of administration include, but are not limited to, mucosal, nasal, parenteral, gastrointestinal, intraspinal, intrauterine, intraocular, intradermal, intracranial, intratracheal, intravaginal, intracerebroventricular, intracerebral, ophthalmic, buccal, epidural and sublingual. Each possibility represents a separate embodiment of the present invention.

In one embodiment, the crystalline forms of the present invention are particularly suitable for oral administration in the form of tablets, capsules, pills, dragees, powders, granules and the like. Each possibility represents a separate embodiment of the present invention. A tablet may be made by compression or molding, optionally with one or more excipients as is known in the art. Specifically, molded tablets may be made by molding in a suitable machine a mixture of the powdered active ingredient moistened with an inert liquid diluent.

In another embodiment, the tablets and other solid dosage forms of the pharmaceutical compositions described herein may optionally be stored or prepared with coatings and shells, such as enteric coatings and other coatings well known in the art. They may also be formulated so as to provide slow or controlled release of the active ingredient therein using, for example, hydroxypropylmethyl cellulose in varying proportions to provide the desired release profile, other polymer matrices and the like. The active ingredient can also be in micro-encapsulated form, if appropriate, with one or more of the above-described excipients.

Uses of Crystalline Forms of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl) succinimide (Compound 1)

In one embodiment, the present invention provides a method of treating cancer comprising administering the composition as described hereinabove to a subject in need. In another embodiment, the cancer is selected from: bladder cancer, breast cancer, colorectal cancer, gastric cancer, head and neck cancer, kidney cancer, liver cancer, lung cancer, non-small cell lung cancer (NSCLC), ovarian cancer, pancreatic cancer, gall bladder cancer, prostate cancer, thyroid cancer, osteosarcoma, rhabdomyosarcom a, malignant fibrous histiocytoma (MFH), fibrosarcoma, glioblastomas/astrocytomas, neuroblastoma, melanoma, T-cell acute lymphoblastic leukemia (T-ALL) and mesothelioma. Each possibility represents a separate embodiment of the present invention.

Definitions

In one embodiment, the term “crystalline” as described herein means a solid form of material having a significant amount or degree of crystallinity (at least 1%, at least 10%, or at least 30% by weight of a crystalline phase). Thus, “crystalline” within the context of the present invention comprises highly crystalline materials as well as semi- or partially-crystalline materials and/or any material having amount or degree of crystallinity of above 1%, above 10% or above 30% and below or equal 100% of crystalline phase by weight.

In one embodiment, the term “therapeutically effective amount” as described herein refers to an amount of an agent which is effective, upon single or multiple dose administration to the subject in providing a therapeutic benefit to the subject. In additional embodiments, the crystalline forms of the present invention are used for the preparation of a medicament for treating the aforementioned diseases or disorders.

In one embodiment, the term “room temperature” (or RT) as described herein refers to temperature range of between 12-35° C., between 20-30° C., between 20-25° C. or between 23-27° C.

In one embodiment, the term “to afford a precipitate” as described herein refers to a process or a step in a process where a precipitate is formed, usually from a solution or a slurry. In one embodiment, the precipitate formation process is immediately following the previous step (e.g. adding anti-solvent to a solution of dissolved compound or mixing/dissolving the compound in a solvent system). In another embodiment, the precipitate formation process may take a few minutes, several minutes, hours or days. Each possibility represents a separate embodiment of the present invention.

In one embodiment, when solvent ratios (e.g. “X:X”) are disclosed, the ratios are volumetric.

While certain features of the present invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the present invention.

EXAMPLES

Example 1: Form Screening

A total of eight forms and patterns were identified for Compound 1: N-2, E2-1/IPA2-1/M3-1 (also referred to as −1 structure), P1, P2, P3, P4, P5, and P6 (FIGS. 1-10).

TABLE 1

Summary of forms/patterns and isolation conditions

| FORM/PATTERN | SLURRY/ POWDER | ISOLATION CONDITION |
|---|---|---|
| N-2 | Slurry/Powder | Acetic Acid/Water, ETOH/water, etc. |
| E2-1/IPA2-1/M3-1 | Slurry | Ethanol, IPA, Methanol; other solvent systems (i.e. THF/heptane, Acetone/heptanes, propylene glycol, etc.) |
| P1 | Powder | Desolvation of E2-1, IPA2-1 and M3-1 |
| P2 | Slurry | P1 slurried in ethyl acetate |
| P3 | Slurry | P1 slurried in acetonitrile |
| P4 | Powder (HTC) | 1:1 MeCN/MTBE, 1:2 DCM/Heptane 1:1 DCM/MTBE and 1:1 MEK/Cyclohexane |
| P5 | Slurry | Recrystallization in Acetone:water (1:1) |
| P6 | Slurry | Recrystallization in Ethanol:water (1:1) |

The N-2 form is a neat form crystallized from e.g. THF/heptanes. Additional conditions of isolating N-2 are summarized in Table 1. E2-1 (diethanolate), IPA2-1 (di-isopropanolate) and M3-1 (tri-methanolate) are alcohol solvates isostructural to N-2, where conditions of isolation thereof are summarized in Table 1. The phase purity is not known for patterns P1-P6. Of the patterns identified to date, only P1 and P4 were obtained from isolated solids and are presumably neat/desolvated phases. The remaining patterns (P2, P3, P5 and P6) were obtained from slurries and never isolated as dry solids. P2 and P3 are presumed solvates which are isostructural with N-2 and convert to N-2 after drying.

HTC (High Throughput Crystallization) Screening for Free Base

Figure 11A:
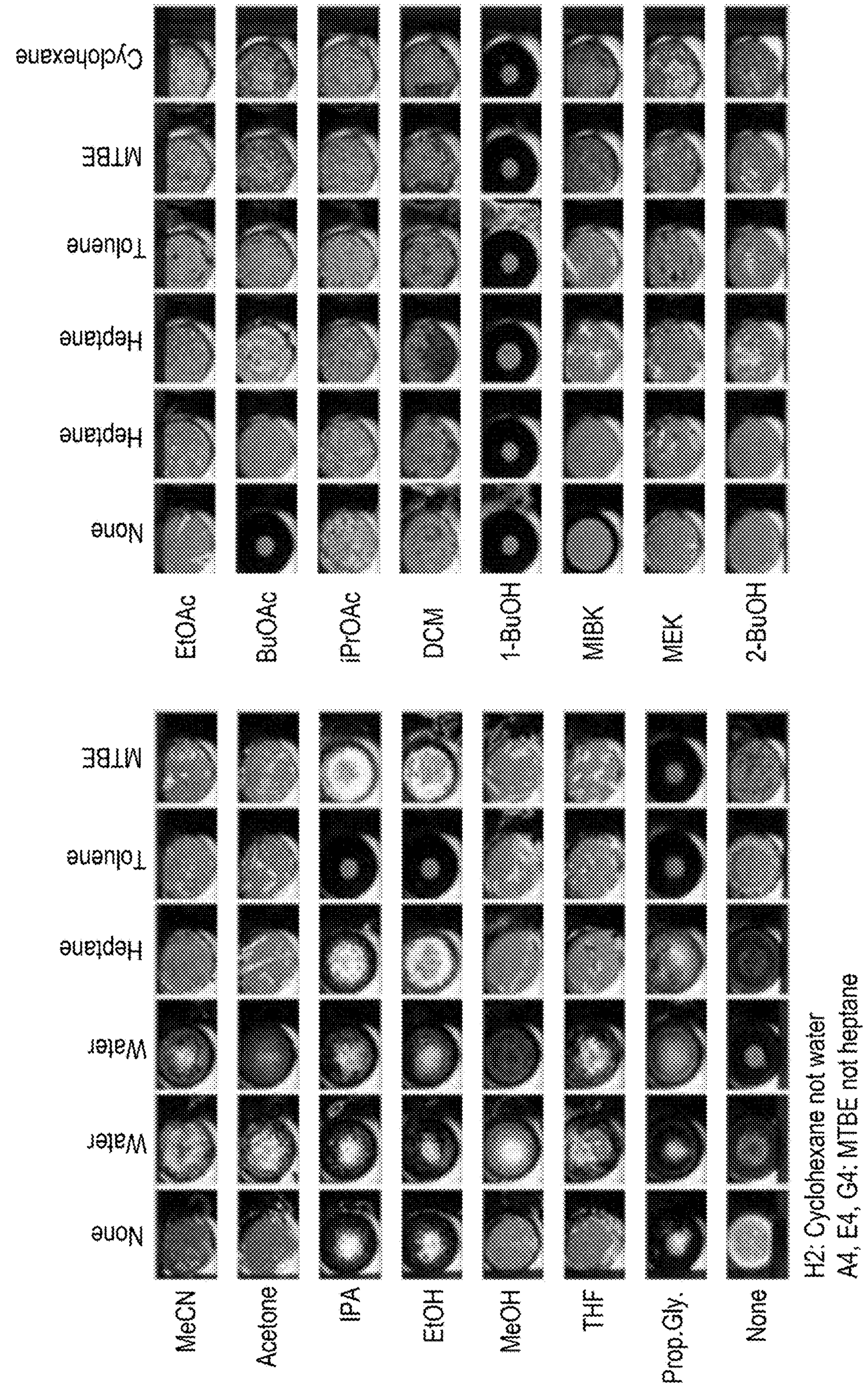
FIGS. 11A-11B depict Compound 1 HTC solvent screen: microscopy images and crystallization solvents for (A) neutral form screen (i.e. neutral plate); and (B) neutral form screen in the presence of weak acids (i.e. co-crystal plate).
Figure 11B:
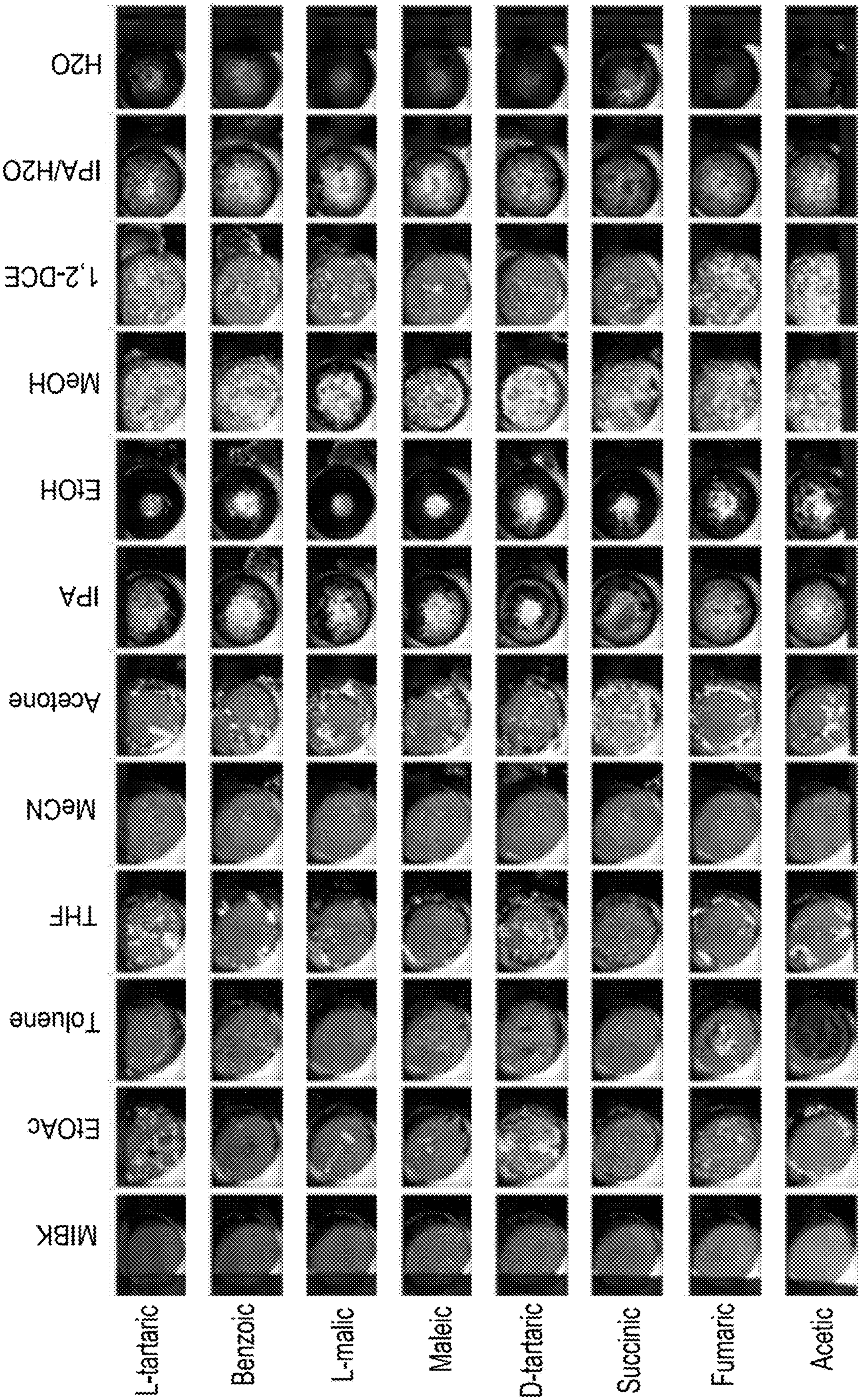

HTC solvent screening was conducted for Compound 1 alone (i.e. neutral plate) and in the presence of weak acids (i.e. cocrystal plate) in a 96 well format (FIGS. 11A-11B). For each plate, 100 mg of material was dissolved at room temperature (RT) in 5 mL of tetrahydrofuran and divided evenly across the 96 wells for the neutral plate (FIG. 11A) and across the eight vials containing 2 equivalents of the each of the weak acids listed in FIG. 11*b* for the cocrystal plate. The standard full plate solvent/anti-solvent array was charged to the neutral plate (refer to FIG. 11A) and the solvents listed in FIG. 11B were charged to the cocrystal plate. Based on the microscopy images, crystallization was apparent in many wells for both plates. The crystallized solids were analyzed by Raman and select wells were also evaluated by GADDS (General Area Detector Diffraction System) and PXRD (Powder X Ray Diffraction) analysis. A new PXRD pattern: P4 was obtained from HTC neutral plate screen from the following solvent systems: MeCN/MTBE, DCM/heptane, DCM/MTBE, and MEK/cyclohexane. From PXRD analysis, N-2, P1, −1 structure, P4 or mixtures of these forms/phase (s) were crystallized from the neutral and cocrystal plates. Several solvent systems gave PXRD patterns similar to IPA2-1/E2-1 (e.g. acetone/water, acetone/MTBE, THF/water, IPAC/heptanes), suggesting that other solvents besides isopropanol, methanol, and ethanol may incorporate in the −1 structure. There was no evidence of cocrystal formation from the HTC cocrystal screen.

Manual Crystallization of Free Base

A manual solvent screen was conducted using 50 mg in 1 mL of the solvents listed in Table 2. Two new unknown patterns, P5 and P6 were identified from recrystallization in acetone:water 1:1 (slurry pattern P5) and ethanol water 1:1 (slurry pattern P6). After drying, P5 and P6 were both converted to N-2. Similar to HTC studies, other solvent systems (e.g. THF/heptane, acetone/heptanes) generated patterns similar to IPA2-1/E2-1/M3-1 in slurry suggesting that other solvents may incorporate in the −1 structure. The N-2 form was observed from several solvent systems, including acetonitrile (slurry), water (slurry and wetcake), DCM (slurry), acetic acid/water (slurry and wetcake), and ethyl acetate (slurry and wetcake).

TABLE 2

Manual screen conditions summary

| SOLVENT SYSTEM | FORM ID/NOTES |
|---|---|
| Ethanol, Ethanol:water 1:2 Rx | 5-day ethanol slurry: IPA2-1/E2-1<br>Rx Ethanol:water 1:2: Amorphous/N-2 |
| Ethanol:Water 1:1 | 5-day slurry: (P6)<br>Dried: N-2 |
| IPA, IPA:water 1:2 Rx | 5-day slurry: IPA2-1<br>Rx IPA:water 1:2: IPA2-1 |
| IPA:Water 1:1 | 5-day slurry: IPA2-1<br>Dried: P1 |
| THF:n-heptane 1:1 Rx | 5-day slurry: IPA2-1<br>Dried: N-2 |
| THF:water 1:1 Rx | ND |
| Acetone:water 1:1 Rx | 5-day slurry: Unknown form (P5)<br>Dried: N-2 |
| Acetone:n-heptane 1:1 Rx | 5-day slurry: IPA2-1<br>Dried: N-2 |
| Water | 5-day slurry: N-2<br>8-day slurry/wet cake: N-2 |
| Ethyl Acetate | 8-day slurry/wet cake: Similar to N-2 |
| DCM | 5-day slurry: N-2 |
| Acetonitrile | 5-day slurry: Similar to N-2 |
| Acetonitrile:water 1:1 | 5-day slurry: N-2 |
| Acetic Acid:water 1:1 | 5-day slurry: N-2<br>Wet cake: N-2 |
| DMSO:water 1:1 | 5-day slurry: Amorphous/N-2 peaks |
| Ethanol Rx | Initial: E2-1/IPA2-1 |
| Ethanol:water 1:1 Rx | Initial: E2-1/IPA2-1/N-2<br>15 min. slurry RT: E2-1/IPA2-1/N-2<br>4-day slurry: E2-1/IPA2-1 |

Example 2: Characterization of Free Base Forms

Characterization of N-2 and P1

Figure 12A:
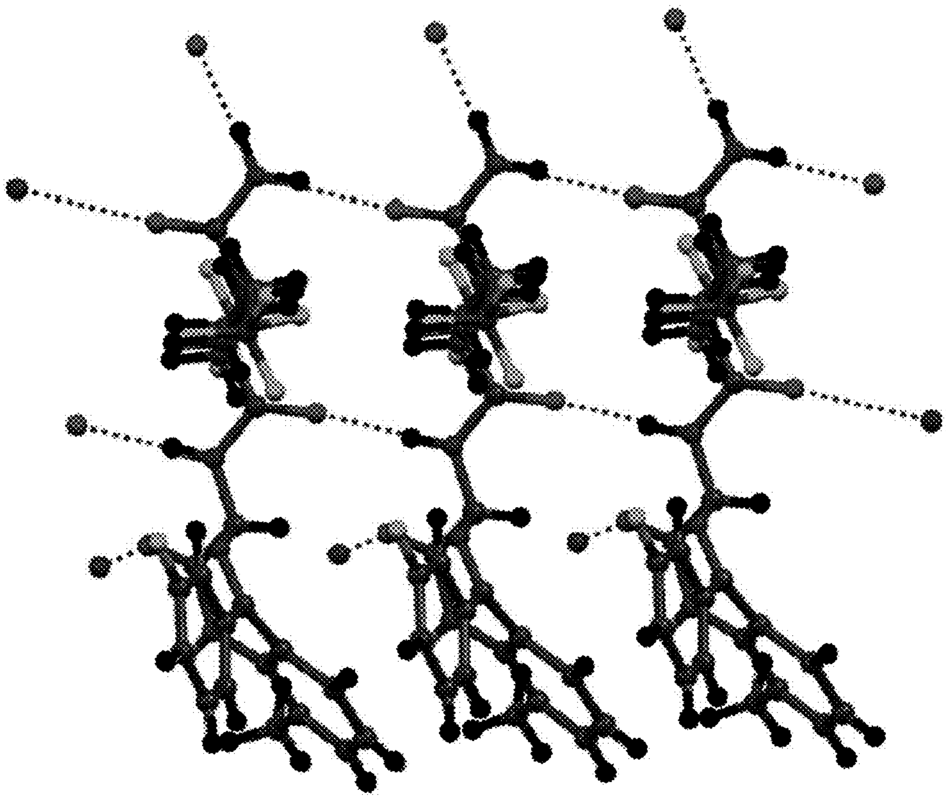
FIGS. 12A-12B depict (A) Selected hydrogen bonds between Compound 1 molecules observed in N-2 form; and B) Packing of Compound 1 molecules parallel to bc-plane in form N-2.
Figure 12B:
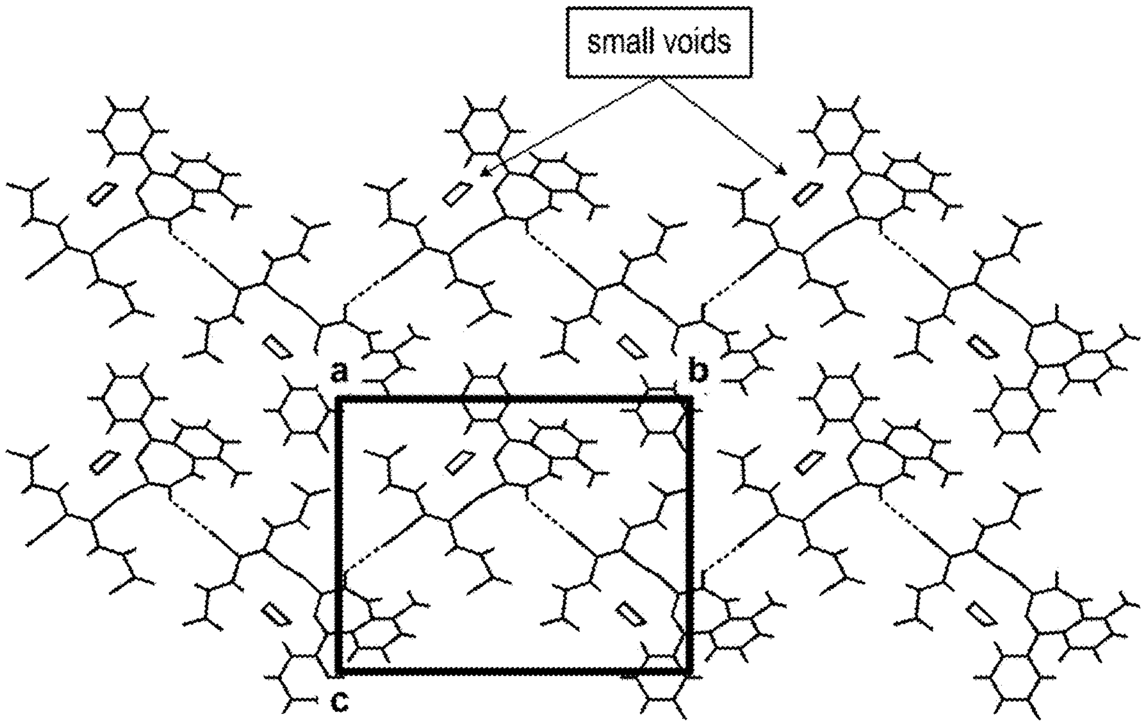
Figure 13:
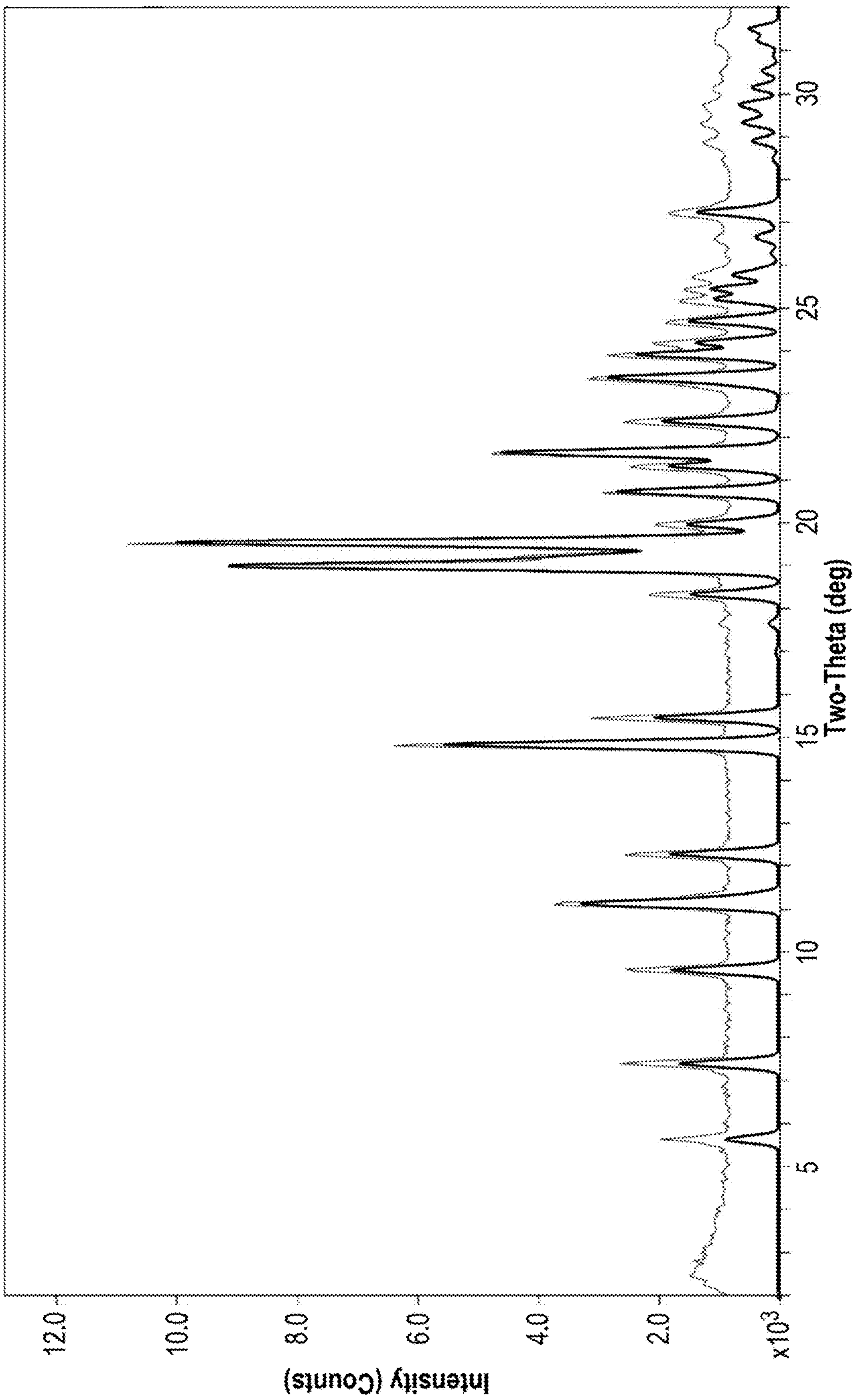
FIG. 13 depicts the PXRD pattern for the N-2 form as dry powder (higher pattern) overlaid with the simulated N-2 pattern at RT (lower pattern).
Figure 14:
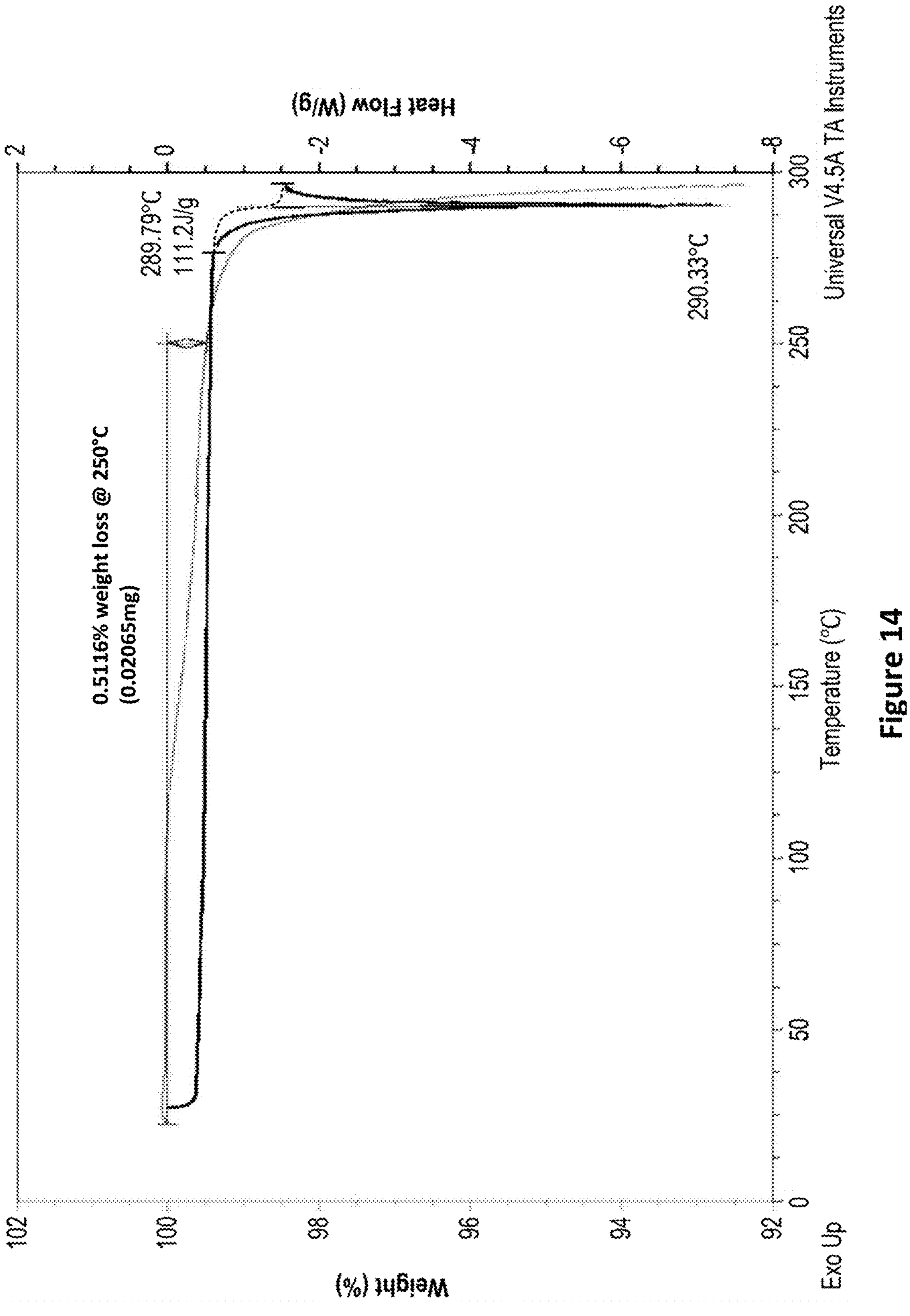
FIG. 14 depicts DSC/TGA thermograms of the P1 form.

The crystal structure for Compound 1 was determined by single crystal X-ray diffraction studies on elongated prismatic crystals grown from THF/heptane. The intermolecular hydrogen-bonding in the N-2 structure is shown in FIGS. 12A-12B; the structure contains small voids of about 20 $Å^3$. The experimental PXRD pattern for N-2 matches the simulated pattern which confirms the single phase identity of N-2 crystallized in bulk (FIG. 13). The slurry and dry PXRD patterns for N-2 match, indicating that N-2 crystallizes directly from solution. Thermal analysis of material representative of N-2 (crystallized from acetic acid:water) shows a melt decomposition at ca. 290° C. with 0.05% weight loss at 250° C. consistent with neat form and the absence of solvent in the structure (FIG. 14). No physical change in form is observed after heating N-2 to 270° C. (FIG. 1).

The free base lots initially crystallized by Discovery Chemistry were either P1 or mixtures of P1 and IPA2-1. P1 is a desolvated phase that has not been observed to crystallize directly from solution. IPA2-1, E2-1 and M3-1 all convert to P1 upon drying. To date, the single crystal structure or ssNMR has not been collected for P1 to confirm that it is a single phase.

Figure 15:
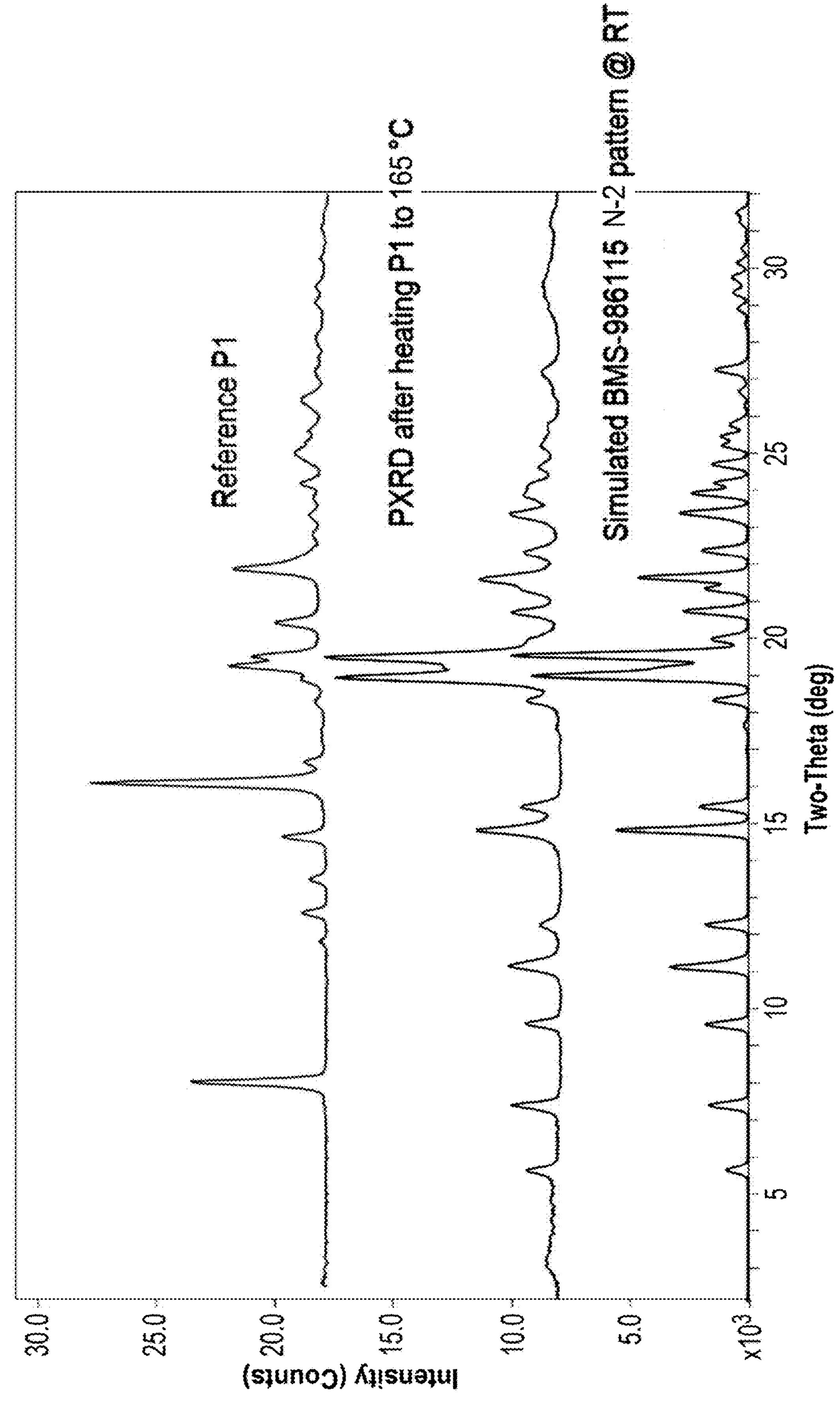
FIG. 15 depicts PXRD patterns of the initial P1 form at room temperature (top); P1 form after heating to 165° C. and then cooling back to room temperature (middle); and the N-2 form at room temperature (bottom).
Figure 16:
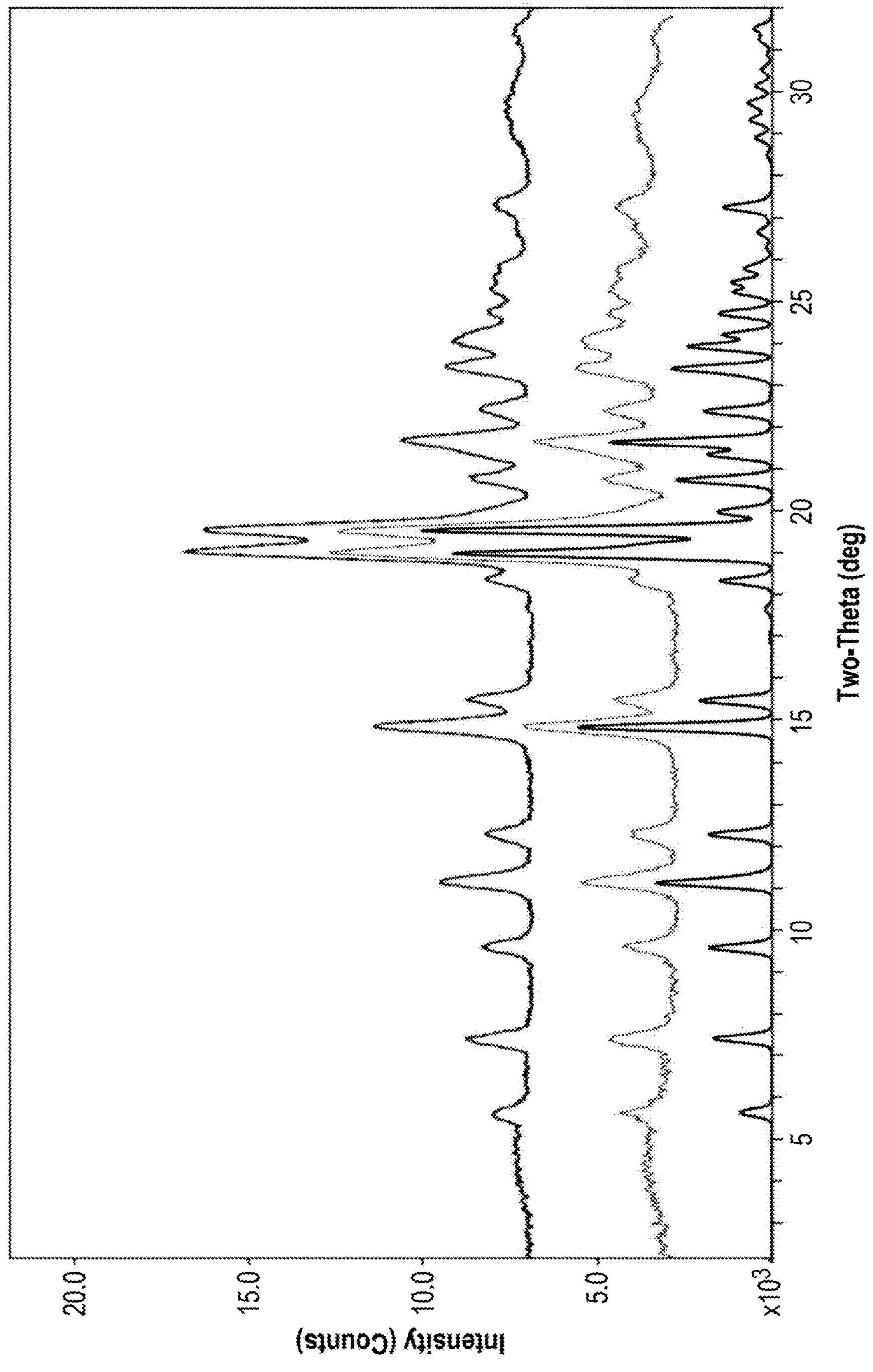
FIG. 16 depicts PXRD patterns of: P1 form following slurrying thereof in FASIF (fasted state simulated intestinal fluid) (top); in HCl (pH=1) (middle); and of N-2 form (bottom).

DSC/TGA data for P1 shows an exothermic transition with an onset at ca 130° C. (FIG. 14). Heating past the exothermic transition to 165° C. results in the formation of N-2, suggesting that P1 and N-2 are monotropically related with N-2 being the more stable form below 290° C. (FIG. 15). Additional experiments confirmed that P1 converts to N-2 on heating past the endothermic transition at 165° C. However, additional peaks were observed on cooling which do not match any of the known crystalline forms/phases. P1 also converts to N-2 after slurrying in aqueous solutions (FIG. 16), which confirms that N-2 is more stable than P1 at RT. Thus, based on thermal data and slurry conversion studies at RT, N-2 and P1 are monotropic with N-2 being the more stable form below 290° C.

Solid State Stability of N-2 Free Base Form

Solid state stability was conducted only on N-2, at 5° C., 25° C., 40° C./75% RH (open and closed), and 50° C. for up to 4 weeks. N-2 was chemically and physically stable at all conditions for up to 4 weeks. N-2 was also chemically and physically stable when exposed to high intensity light (HIL)/ultraviolet (UV) light for 7 days, indicating that handling thereof under ambient conditions should not be a concern.

Example 3: Preparation of N-2

N-2 was first scaled-up (1.4 g) through a recrystallization in acetone:water 1:1.5 with a yield of 89%. However, in this solvent system, N-2 is generated through desolvation of a presumed acetone solvate: P5. Recrystallizations in the ternary solvent systems: acetic acid: ethanol: water (1:1:3) gave N-2 in slurry while acetic acid:IPA:water (1:1:3) gave the IPA2-1 solvate. These solvent systems were not ideal since both have the potential of forming the IPA2-1/E2-1 solvate depending on the corresponding solvent activity. A direct crystallization method was evaluated based on manual screening studies which showed that N-2 crystallizes directly from several solvent systems (e.g. acetonitrile/water, DCM and acetic acid/water). Since several patterns have been observed from acetonitrile/water, i.e. P3 and N-2, the crystallization method development focused on acetic acid:water as the recrystallization solvent.

For IND (Investigational New Drug) toxicology and First-in-human (FIH) batches, the API (Active Pharmaceutical Ingredient) is isolated from reaction mixture consisting of DMF/water and recrystallized from acetic acid: water (1:2.5). The current crystallization procedure involves first completely dissolving API in acetic acid (5 mL/g) and adding water (12.5 ml/g) as an anti-solvent. The resulting slurry is stirred for 2 hours at room temperature, filtered and washed with water (2×3 ml/g) and dried at 50° C. The form obtained was confirmed to be N-2 by GADDS/PXRD.

Alternatively, the API is isolated from reaction mixture consisting of DMF/water and recrystallization from acetic acid: water (1:1.1). API is completely dissolved in acetic acid (5 mL/g) and water (5.5 mL/g) is added as an anti-solvent. The resulting slurry is stirred for 10-20 minutes at 15-25° C., filtered and washed with water (2×5 mL/g) and dried at 50° C. The form obtained was confirmed to be N-2 by GADDS/PXRD.

Example 4: Solubility and Bioavailability

N-2 has an aqueous solubility of <1 μg/mL in water. Of the solvents tested, the solubility of N-2 was greatest in PEG 400 (~38 mg/mL) and higher molecular weight PEGs. Slurrying N-2 in propylene glycol gave a PXRD pattern similar to the simulated pattern for −1 type structures, suggesting that Compound 1 forms a solvate with propylene glycol which is isostructural with E2-1/IPA2-1/M3-1.

Oral absorption of Compound 1 was found to be influenced by solubility, dissolution rate, precipitation inhibitor content in the formulation, and efflux mediated permeability. When dosed as a solution in ethanol/TPGS/PEG 300 (10/10/80 v/v/v), the oral bioavailability of Compound 1 in mice (2 mg/kg), rats (5 mg/kg), dogs (0.1 mg/kg) and monkeys (0.2 mg/kg) is 51%, 18%, 62% and 25%, respectively. However, when Compound 1 is dosed as a microsuspension with d90 of 3 μm in 2% polyvinyl pyrrolidone and 0.15% docusate sodium in water, the oral bioavailability in rats (5 mg/kg) is ~1%. Dosed as an amorphous solid with hypromellose acetate succinate, the oral bioavailability of Compound 1 in rats (5 mg/kg) is ~5%. Compound 1 is a substrate for efflux transporter (efflux ratio ~9 in caco2 assay at 3.7 μM). The bioavailability of Compound 1 in rats dosed 5 mg/kg is increased to 100% with coadministration of Elacridar.

A solubilized capsule formulation was used to support FIH studies, because Compound 1 has low intrinsic aqueous solubility, poor oral absorption when dosed as a microsuspension, and a classification of Band 5 special.

Example 5: Alternative Synthesis of the N-2 Form

Form N-2 was also prepared as follows:

Compound 1 was added to a reactor under nitrogen;

4.0 mL/g equivalent of acetic acid was added to the reactor;

the contents of the reactor were adjusted to 20±5° C.;

the contents of the reactor were agitated at 20±5° C. until all solids dissolved;

the contents of the reactor were transferred across a polish filter;

1.0 mL/g equivalent of acetic acid was added to the reactor;

the contents of the reactor were transferred across a polish filter;

the combined polish filtrates were transferred back to the reactor;

5.5 g/g equivalents of water were added to the reactor at a rate that maintains the internal temperature at ≤25° C.;

the product in the reactor was isolated by vacuum filtration;

8.74 g/g equivalents of water were added to the reactor;

the contents of the reactor were transferred to a filter;

8.74 g/g equivalents of water were added to the reactor;

the contents of the reactor were transferred to a filter;

the product from the filter was transferred to a drying tray;

the product was dried at 50±5° C. until a constant weight was obtained;

the product was sampled and tested by HPLC for residual acetic acid and water content; and the dried product was put in an appropriate container and labeled.

Figure 17:
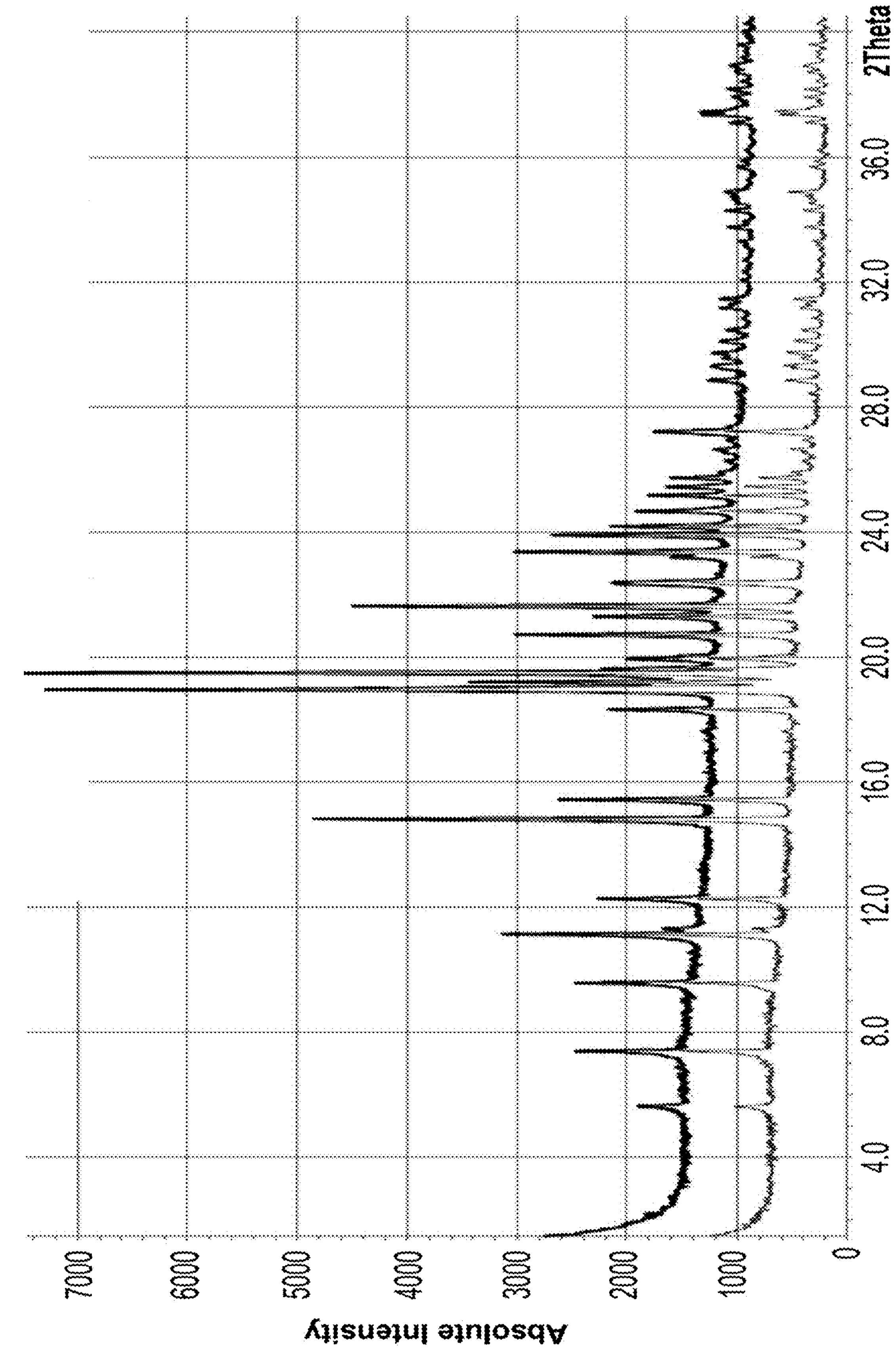
FIG. 17 depicts an overlay of PXRD patterns of the N2 form, prepared according to the procedure described in Example 5: top tracing: reference standard; bottom tracing: sample.
Figure 18:
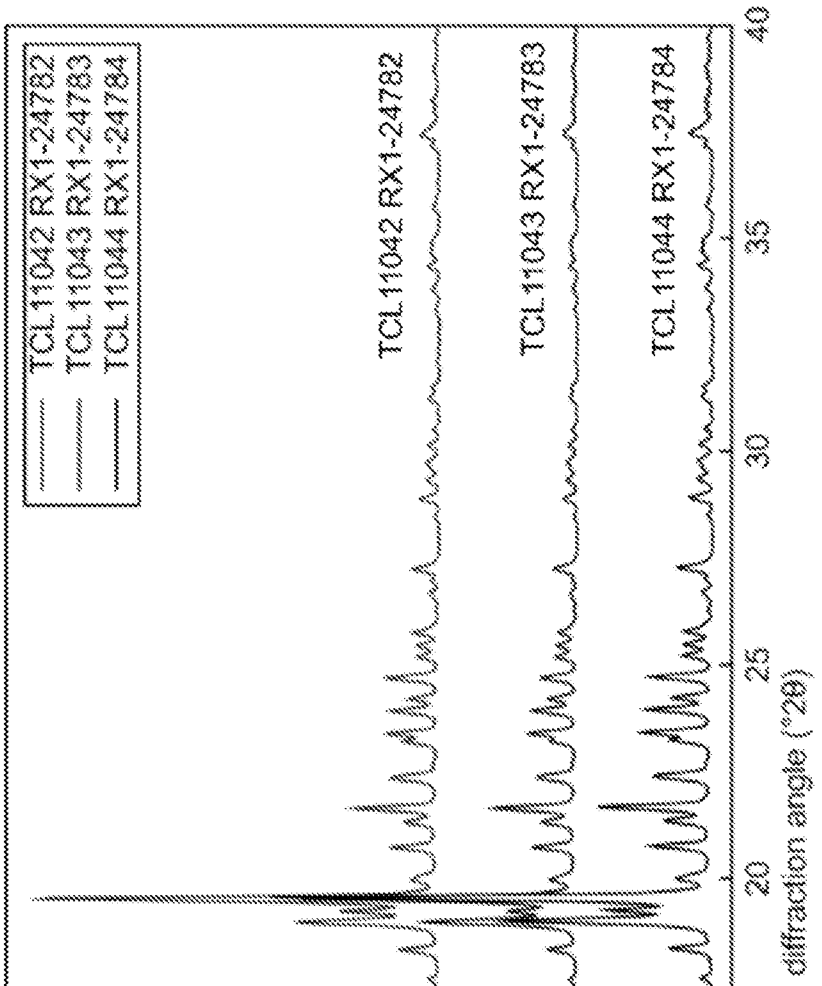
FIG. 18 depicts an overlay of PXRD patterns of the N2 form, prepared according to the procedure described in Example 5: top tracing: reference standard; middle tracing: sample 1; bottom tracing: sample 2.

The crude Compound 1 dissolved in acetic acid was polish filtered using a disc filter, PTFE 0.45 μM disposable filter and a 3-piece Hydradyne 1 μM membrane. The obtained dried product from several different batches was characterized by XRPD and had a diffractogram corresponding to the N-2 form (FIGS. 17-18). NMR, MS, FTIR and HPLC showed that the obtained compound batches characterized in FIG. 18 is Compound 1. HPLC showed that assay purity was between 98.3-101.7% (corrected for water, total volatiles and acetic acid content). Particle size distribution showed X10=3.3 μm, X50=11.3 μm and X90=45.7 μm for one batch and X10=3.2 μm, X50=12.2 μm and X90=33.4 μm for the second batch. The data demonstrated high batch to batch reproducibility.

What is claimed is:

1. A crystalline form of (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl) succinimide, represented by the structure of Compound 1:

(1)

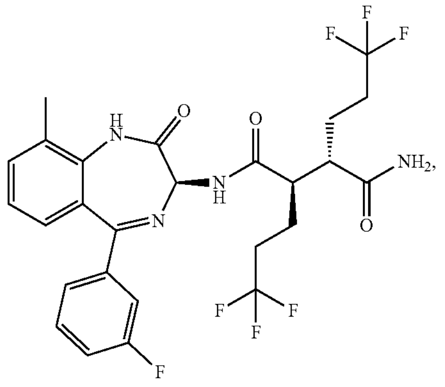

wherein the crystalline form comprises a. N-2 crystalline form, M3-1 crystalline form, P2 crystalline form, P3 crystalline form, P4 crystalline form, P5 crystalline form, P6 crystalline form, or any combination thereof;

b. P2 crystalline form, crystallized from crystalline form P1 which was slurried in ethyl acetate;

c. P3 crystalline form, crystallized from crystalline form P1 which was slurried in acetonitrile;

d. P1 crystalline form, crystallized via desolvation of IPA2-1 or M3-1; or e. IPA2-1 crystalline form, crystallized from isopropyl alcohol (IPA).

2. The crystalline form of claim 1, wherein the crystalline form comprises the N-2 crystalline form.

3. The crystalline form of claim 2, wherein said N-2 crystalline form is crystallized from ethanol/water.

4. The crystalline form of claim 2, wherein said N-2 crystalline form is prepared via dissolution of Compound 1 in acetic acid followed by addition of water which results in crystallization of Compound 1.

5. The crystalline form of claim 2, wherein said crystalline form N-2 is characterized by an XRPD pattern having peaks at 14.92±0.3, 15.49±0.3, 19.3±0.3, 19.64±0.3 and 21.57±0.3 degrees two theta (2q); or characterized by unit cell parameters of a=4.84±0.3 Å, b=18.47±0.3 Å, c=15.67±0.3 Å, a=90°, b=91.62±0.5°, g=90°, unit cell volume is 1399.51±0.5 $Å^3$, number of compound per asymmetric unit is 1 and space group is $P2_1$.

6. The crystalline form of claim 5, characterized by said XRPD pattern which has additional peaks at 11.12±0.3 and 12.23±0.3 degrees two theta (2q).

7. The crystalline form of claim 1, wherein the crystalline form comprises the IPA2-1 crystalline form, crystallized from isopropyl alcohol (IPA).

8. The crystalline form of claim 7, wherein said IPA2-1 crystalline form is characterized by an XRPD pattern having peaks at 7.71±0.3, 12.96±0.3, 13.12±0.3, 14.84±0.3 and 19.35±0.3 degrees two theta (2q); or characterized by unit cell parameters of a=11.93±0.3 Å, b=8.57±0.3 Å, c=17.42±0.3 Å, a=90°, b=105.16±0.5°, g=90°, unit cell volume is 1718.67±0.5 $Å^3$, number of compound per asymmetric unit is 1 and space group is $P2_1$.

9. The crystalline form of claim 8, characterized by said XRPD pattern which has additional peaks at 21.62±0.3 and 21.83±0.3 degrees two theta (2q).

10. The crystalline form of claim 1, wherein the crystalline form comprises the M3-1 crystalline form.

11. The crystalline form of claim 10, wherein said M3-1 crystalline form is crystallized from methanol.

12. The crystalline form of claim 10, wherein said crystalline form M3-1 is characterized by an XRPD pattern having peaks at 7.96±0.3, 13.26±0.3, 19.19±0.3 and 21.56±0.3 degrees two theta (2q); or characterized by unit cell parameters of a=11.72±0.3 Å, b=8.36±0.3 Å, c=17.41±0.3 Å, a=90°, b=108.62±0.5°, g=90°, unit cell volume is 1616.59±0.5 $Å^3$, number of compound per asymmetric unit is 1 and space group is $P2_1$.

13. The crystalline form of claim 1, wherein the crystalline form comprises the P4 crystalline form.

14. The crystalline form of claim 13, wherein said P4 crystalline form is crystallized from v/v 1:1 MeCN/MTBE, 1:2 DCM/Heptane, 1:1 DCM/MTBE or 1:1 MEK/Cyclohexane.

15. The crystalline form of claim 13, wherein said crystalline form P4 is characterized by an XRPD pattern having peaks at 7.16±0.3, 16.02±0.3, 18.62±0.3, 20.32±0.3 and 21.14±0.3 degrees two theta (2q).

16. The crystalline form of claim 15, characterized by said XRPD pattern which has additional peaks at 12.04±0.3 and 23.56±0.3 degrees two theta (2q).

17. The crystalline form of claim 1, wherein the crystalline form comprises the P5 crystalline form.

18. The crystalline form of claim 17, wherein said P5 crystalline form is crystallized from acetone:water 1:1 v/v.

19. The crystalline form of claim 17, wherein said crystalline form P5 is characterized by an XRPD pattern having peaks at 6.5±0.3, 10.99±0.3, 17.36±0.3, 19.49±0.3 and 21.84±0.3 degrees two theta (2q).

20. The crystalline form of claim 19, characterized by said XRPD pattern which has additional peaks at 14.78±0.3 and 20.26±0.3 degrees two theta (2q).

21. The crystalline form of claim 1, wherein the crystalline form comprises the P6 crystalline form.

22. The crystalline form of claim 21, wherein said P6 crystalline form is crystallized from ethanol: water 1:1 v/v.

23. The crystalline form of claim 21, wherein said crystalline form P6 is characterized by an XRPD pattern having peaks at 3.52±0.3, 10.00±0.3, 12.36±0.3, 19.32±0.3 and 20.40±0.3 degrees two theta (2q).

24. The crystalline form of claim 23, characterized by said XRPD pattern which has additional peaks at 14.2±0.3 and 16.04±0.3 degrees two theta (2q).

25. The crystalline form of claim 1, wherein said crystalline form P1 is characterized by an XRPD pattern having peaks at 8.04±0.3, 14.64±0.3, 16.1±0.3, 19.52±0.3 and 21.94±0.3 degrees two theta (2q).

26. The crystalline form of claim 25, characterized by said XRPD pattern which has additional peaks at 20.46±0.3 and 25.1±0.3 degrees two theta (2q).

27. The crystalline form of claim 1, wherein said crystalline form P2 is characterized by an XRPD pattern having peaks at 7.35±0.3, 14.61±0.3, 19.2±0.3, 23.15±0.3 and 26.4±0.3 degrees two theta (2q).

28. The crystalline form of claim 27, characterized by said XRPD pattern which has additional peaks at 11.04±0.3 and 23.71±0.3 degrees two theta (2q).

29. The crystalline form of claim 1, wherein said crystalline form P3 is characterized by an XRPD pattern having peaks at 7.45±0.3, 14.76±0.3, 19.02±0.3, 19.44±0.3 and 21.41±0.3 degrees two theta (2q).

30. The crystalline form of claim 29, characterized by said XRPD pattern which has additional peaks at 11.11±0.3 and 22.15±0.3 degrees two theta (2q).

31. A pharmaceutical composition comprising a therapeutically effective amount of the crystalline form according to claim 1, and a pharmaceutically acceptable carrier.

32. The composition of claim 31, wherein the composition is in a solid state, suspension or emulsion form.

33. The composition of claim 32, wherein the composition is in a solid-state form; and the composition is a tablet.

34. The composition of claim 32, wherein the composition is a suspension.

35. The composition of claim 34, wherein the suspension comprises the crystalline form and propylene glycol.

* * * * *